(12) United States Patent
Bruno et al.

(10) Patent No.: US 8,318,920 B2
(45) Date of Patent: Nov. 27, 2012

(54) THERAPEUTIC NUCLEIC ACID-3'-CONJUGATES

(75) Inventors: John G. Bruno, San Antonio, TX (US); Judson C. Miner, San Antonio, TX (US)

(73) Assignee: Operational Technologies Corporation, San Antonio, TX (US)

( * ) Notice: Subject to any disclaimer, the term of this patent is extended or adjusted under 35 U.S.C. 154(b) by 776 days.

(21) Appl. No.: 11/735,221

(22) Filed: Apr. 13, 2007

(65) Prior Publication Data

US 2008/0161236 A1    Jul. 3, 2008

Related U.S. Application Data

(63) Continuation-in-part of application No. 11/058,054, filed on Feb. 15, 2005, now Pat. No. 7,910,297.

(60) Provisional application No. 60/548,629, filed on Feb. 27, 2004.

(51) Int. Cl.
C07H 21/04    (2006.01)
(52) U.S. Cl. ................... 536/24.5; 536/24.31; 536/24.1; 435/6; 435/325; 435/375
(58) Field of Classification Search .................. None
See application file for complete search history.

(56) References Cited

U.S. PATENT DOCUMENTS

| | | | |
|---|---|---|---|
| 5,270,163 | A | 12/1993 | Gold et al. |
| 5,475,096 | A | 12/1995 | Gold et al. |
| 5,573,913 | A | 11/1996 | Rosemeyer et al. |
| 6,127,119 | A | 10/2000 | Stephens et al. |
| 6,172,208 | B1 | 1/2001 | Cook |
| 6,235,886 | B1 | 5/2001 | Manoharan et al. |
| 6,566,343 | B2 | 5/2003 | Biesecker et al. |
| 6,623,926 | B1 | 9/2003 | Lohse et al. |
| 6,780,850 | B1 | 8/2004 | Dougan et al. |

OTHER PUBLICATIONS

Chu, Ted, C., et al.; Aptamer: Toxin Conjugates that specifically target prostate tumor cells: Cancer Research: Jun. 15, 2006: pp. 5989-5992; 66(12): American Association for Cancer Research; Austin, TX, US.
Abe, Ikuro et al.; Enzymatic formation of unnatural cytokinin analogs by adenylate isopentenyltransferase from mulberry; Science Direct: Feb. 15, 2007; pp. 795-800; Biochemical and Biophysical Research Communications 355.
Zahler, Alan M. et al.; Telomere terminal transferase activity in the hypotrichous ciliate Oxytricha nova and a model for replication of the ends of linear DNA molecules; Nucleic Acids Research; 1988; pp. 6953-6972: IRL Press Ltd.; Oxford, England.
Bell et al.,"Oligonucelotide NX1838 inhibits VEGF165-mediated cellular responses In vitro"; In vitro Cell Develop. Biol. Animal (1999) 35: 533-542.
Biesecker, et al, :Derivation of RNA Aptamer inhibitors of Human Complement C5, Immunopharm (1999) 42:219-230.

Blank, et al. "Systematic Evolution of a DNA Aptamer Binding to Rat Brain Tumor Microvessels, Selective Targeting of Endothelial Regulatory Protein Pigpen," J. Biol. Chem. (2001) 276:16464-16468.
Brody, E.N. and Gold, L., "Aptamers as Therapeutic and Diagnostic Agents," Reviews in Mol. Biotechnol. (2000), 74:5-13.
Bruno, In Vitro Selection of DNA to Chloroaromatics Using Magnetic Microbead-Based Affinity Separation and Fluorescence Detection, Biochem. Biophys. Res. Comm. (1997) 234: 117-120.
Bruno and Kiel, "In Vitro Selection of DNA Aptamers to Anthrax Spores with Electrochemiluminescence Detection,"Biosensors & Bioelectronics (1999) 14:457-464.
Bruno and Kiel, "Use of Magnetic Beads in Selection and Detection of Biotoxin Aptamers by ECL and Enzymatic Methods," Bio Techniques (2002) 32:178-183.
Dougan, et al., "Extending the Lifetime of Anticoagulant Oligodeoxynucleotide Aptamers in Blood," Nuclear Med. Biol. (2000) 27:289-297.
Drolet, et al., "Pharmacokinetics and Safety of Anti-Vascular Endothelial Growth Factor Aptamer (NX1838) Following Injection into the Vitreous Humor or Rhesus Monkeys." (2000) Pharm. Res. 17:1503-1510.
Hicke, et al., "Tenascin-C Aptamers are generated Using Tumor Cells and Purified Protein," J. Biol. Chem. (2001) 276:48644-48654.
Homann and Goringer, "Uptake and Intracellular Transport of RNA Aptamers in African Trypanosomes Suggest Therapeutic "Piggy-Back" Approach," Bioorg. Med. Chem (2001) 9:2571-2580.
Huang, et al. "Highly Specific Antiangiogenic Therapy is Effective in Suppressing Growth of Experimental Wilms Tumors," J. Pediatric Surg. (2001) 36:357-361.
Murphy, et al., "An Improved Method for the In Vitro Evolution of Aptamers and Applications in protein Detection and Purification," Nucleic Acids Res. (2003) 31:e110-e118.
Ono, T, et al., "2-Fluoro Modified Nucleic Acids: Polymerase-Directed Synthesis, Properties and Stability to Analysis by Matrix Assisted Laser Desorption/Ionization Mass Spectrometry." Nucl. Acids Res. (1997), 25:4581-4588.
Ruckman, J., et al., 2-Fluoropyrimidine RNA-Based Aptamers to the 165 Amino Acid Form of Vascular Endothelial Growth Factor (VEGF 165) J. Biol. Chem. (1998) 273:20556-20567.
Ulrich, Et al., "In Vitro Selection of RNA Aptamers that Bind the Cell Adhesion Receptors of *Trypanosome cruzi* and inhibit cell invasion," J. Biol. Chem. (2002) 277:20756-20762.
Welkos, et al., "The Role of Antibodies to *Bacillus anthracis* and Anthrax toxin components in Inhibiting the Early Stages of Inflection of Anthrax Spores," Microbiology (2001), 147:1677-1685.
Alderson, Formaldehyde-induced mutagenesis: a novel mechanism for its action; Mutation Research, 154 (1985) 101-110.
Anorbe, Perturbation of the NH2 pKa Value of Adenine in Platinum(II) Complexes: Distinct Stereochemical Internucleobase Effects; Chem. Eur. J. (2004), 10:1046-1057.

(Continued)

*Primary Examiner* — Kimberly Chong
(74) *Attorney, Agent, or Firm* — Winstead PC

(57) ABSTRACT

Methods are described for improvement of the serum half life of therapeutic nucleic acids by 3' conjugation to useful target proteins, or other large molecules with useful function. In one embodiment, a 3' A, C or G overhang is added to ds-DNA and the primary amines conjugated using biocompatible bifunctional linkers to proteins. The resulting nucleic acid-3'-conjugates are serum nuclease-resistant and retained in vivo for long periods without rapid kidney clearance. Further, the choice of conjugate imparts additional functionality to the nucleic acid-3-conjugate.

11 Claims, 7 Drawing Sheets

OTHER PUBLICATIONS

Dolan, Robust and effecient synthetic method for forming DNA microarrays; Nucleic Acids Research, 2001, vol. 29, No. 21 e107.

Gacesa; The Immobolization of Adenine Nucleotides on Polysaccharides by using Glutaraldehyde Coupling and Borohydride Reduction; Biochem. J. (1978) 175, 349-352.

Harrison, Site-Specific Methylation of Adenine in the Nuclear Genome of a Eucaryote, *Tetrahymena thermophila*; Molecular and Cellular Biology, Jul. 1986, p. 2364-2370.

Hayatsu, N-Sulfomethylation of guanine, adenine and cytosine with formaldehyde-bisulfite. A selective modification of guanine in DNA; Nucleic Acids Research, vol. 10 No. 20 1982.

Hopwood, The reactions of glutaraldehyde with nucleic acids; Histochemical Journal, 7 (1975), 267-276.

Kloepfer, Uptake of CdSe and CdSe/ZnS Quantum Dots into Bacteria via Purine-Dependent Mechanisms; Applied and Environmental Microbiology, May 2005, p. 2548-2557, vol. 71, No. 5.

Matsuura, Facile Synthesis of Stable and Lectin-Recognizable DNA-Carbohydrate Conjugates via Diazo Coupling, Bioconjugate Chem. 2000, 11, 202-211.

Pues, Functional Roles of the Conserved Aromatic Amino Acid Residues at Position 108; Biochemistry 1999, 38, 1426-1434.

Rall, Evidence for Cross-Linking of Cyclic AMP to Constituents of Brain Tissue by Aldehyde Fixatives: Potential Utility in Histochemical Procedures; Journal of Cyclic Nucleotide Research 8(4): 243-265 (1982).

Scavetta, Structure of Rsrl methyltransferase, a member of the N6-adenine B class of DNA methyltransferases; 3950-3961, Nucleic Acids Research, 2000, vol. 28, No. 20.

Wang, Catalytic Mechanism of Hamster Arylamine N-Acetyltransferase 2, Biochemistry 2005, 44, 11295-11306.

Yamazaki, A New Method of Chemical Modification of N6-Amino Group; Eur. J. Biochem 92, 197-207 (1978).

Zhou, Universal TA Cloning; Curr. Issues Mol. Biol. (2000) 2(1): 1-7.

THERAPEUTIC NUCLEIC ACID-3'-CONJUGATES

PRIOR RELATED APPLICATIONS

This patent application claims priority, as a continuation-in-part, to U.S. Non-provisional Application Ser. No. 11/058,054, filed Feb. 15, 2005 which claims priority to U.S. Provisional Application Ser. No. 60/548,629, filed on Feb. 27, 2004, the disclosures of which are incorporated by reference in their entirety herein.

FIELD OF THE INVENTION

The present invention relates to the field of nucleic acid-based therapeutics where nucleic acid stability and retention are improved by a 3' conjugation to a therapeutic protein. More specifically, the present invention relates to methods for production of aptamers, antisense and other nucleic acid based therapeutics that are blocked at their 3' ends. The 3' blocked nucleic acids have surprisingly increased stability, increased retention in the body, and with the judicious selection of conjugate can have additional therapeutic benefit as well.

BACKGROUND OF THE INVENTION

Aptamers, derived from the latin aptus, meaning, 'to fit', are oligonucleotides that have a specific three dimensional shape and consequent biological activity. Aptamers are generally produced through a process named "systematic evolution of ligands by exponential enrichment" or "SELEX," which is an iterative selection and amplification process. Nucleic acids that bind to a target are selected (non-binders are simply washed away) and then subjected to a round of amplification. As this process is iterated, tightly binding aptamers are enriched in the population, and extremely tight and specific binding between the aptamer and the target can be achieved. The reader is referred to U.S. Pat. No. 5,270,163 and the very large family of related patents for detailed SELEX protocols.

The extraordinary capacity of aptamers to bind tightly to specific targets underlines their tremendous potential as molecular therapeutics. For example, aptamers can be used to selectively target cells (such as tumor cells or pathogens) for death.

For example, U.S. Pat. No. 6,566,343 discusses the potential for aptamers directed at cell surface components of bacteria, cancer cells and parasites to activate the complement system and bring about the lysis of target cells. The patent discloses the linkage of two aptamers—one directed against the target cell and a second one against a component of the complement system (thus recruiting the complement cascade to the target cell)—to achieve complement activation and targeted cell death.

There are two distinct disadvantages to this approach. First, the aptamer-aptamer conjugates are subject to degradation from serum nucleases and second, the aptamer-aptamer conjugates are subject to rapid clearance by the kidneys. Thus, although aptamers are a powerful targeting system, in vivo nucleic acid stability remains a problem.

A Canadian team of researchers (Dougan et al., 2000) demonstrated that 3'-biotinylation of DNA significantly increased its resistance to serum nuclease activity. This was presumably due to steric hindrance and suggests that any 3' or 5' capping or nucleic acid modification should improve nucleic acid stability in vivo.

However, our research surprisingly indicates that 5'-biotinylation is not very effective against serum degradation of DNA, nor is the incorporation of 2'-Fluoro modified deoxynucleotide triphosphates (2'F-dNTPs). Thus, the stability issue is not as simply addressed as one might predict. Hence, improved methods of stabilizing nucleic acids for in vivo therapeutic use are still needed and the invention addresses this problem.

BRIEF SUMMARY OF THE INVENTION

The invention presents a novel means to conjugate nucleic acid at its 3' end to proteins or other large macromolecules (e.g., polyethylene glycols, nanotubes, and the like). The 3' conjugation inhibits the action of serum nucleases that would otherwise rapidly breakdown the DNA in blood, and it dramatically increases retention of the aptamers in blood, which would otherwise be rapidly filtered out by the kidneys.

Various embodiments of the invention allow for the production of aptamers, antisense and other nucleic acid based therapeutics that are blocked at their 3' ends with therapeutic proteins and therapeutic uses for the nucleic acid-3'-conjugates. Generally speaking, ds-DNA is conjugated at its 3' end, followed by conversion to single strand (ss) DNA-3'-conjugates. The 3' conjugates show remarkable serum nuclease resistance and retention in the body and exhibit enhanced therapeutic efficacy as compared with same DNA in a naked (unconjugated) form, due to enhanced stability in vivo.

Various embodiments of the conjugation require the addition of adenine (A), cytosine (C), or guanine (G) to the 3' end of double strand (ds) DNA by means of various enzymes (thymine has no free primary amine group). In particular, *Thermus aquaticus* (Taq) DNA polymerase adds a 3'-A overhang during the PCR process and the template independent enzyme terminal deoxynucleotide transferase (TdT) can add A, C, or G to the 3' end of blunt ended ds-DNA, if only A, C, and G are supplied (i.e., no thymine is provided). In various embodiments, with TdT, the undesired complementary strand will become conjugated to the protein as well, but it will be nonfunctional and nonallergenic, because DNA is of low immunogenicity.

Free primary amines in the terminal A, C, or G's can then be used to link the DNA to a protein (or other conjugate) via a bifunctional linker with an N-hydroxy-succinimide or other suitable functionality. The conjugate is specifically added to the 3' overhang because the remainder of the DNA molecule is double-stranded and cannot participate in conjugation.

After conjugation, the ds-DNA is converted to ss-DNA by means of heating beyond the DNA's melting temperature ($T_m$) for a brief period. Care should be taken to avoid protein denaturation during the melting step. Melting is followed by purification of the ss-DNA-3'-conjugate by chromatographic or other physical and chemical means including affinity separation methods, differential or density centrifugation, and preparative electrophoresis.

Such aptamer-3'-conjugates have a variety of applications. A key application is the targeted killing of pathogens or tumor cells. For example, if the protein conjugate is human or animal C1qrs (or some portion of the complex) it will activate the complement cascade as shown herein, thus targeting the cell for destruction by the immune system. The C1qrs is delivered to the target cell by virtue of being coupled to an aptamer specific for that cell.

Alternatively, one can couple aptamers to carbon nanotubes or other types of nanotubes to bind the surface of an undesirable target cell and kill it by puncturing the cell membrane or cell wall with the attached nanotube. To be effective at killing, aptamer-3'-nanotube conjugates would require energy input via a molecular motor driven by adenosine triphosphate (ATP), creatine phosphate, or other innovative means of energetically driving the nanotube into the target cell membrane to puncture and lyse the target cell.

Another key application of aptamer-3'-conjugates is the neutralization of toxins (e.g., botulinum toxins, cholera and diphtheria toxins, digitalis, ricin, staphylococcal enterotoxins, etc.) by use of specifically developed ss-aptamers linked to serum albumin (SA) to prevent aptamer breakdown and clearance from the blood. The aptamer-3'-SA binds tightly to the toxin, thus neutralizing its effect.

Coupling of aptamers to the complement system could be advantageous in the killing of antibiotic-resistant bacteria, cancer cells, parasites and other target cells. Carbon nanotubes, toxins, and destructive enzymes might also be coupled to the 3'-end of aptamers to create highly effective and long-lived therapeutics against invading cells or target cells.

A greater understanding of the present invention may be had from reference to the following detailed description and the appended claims.

BRIEF DESCRIPTION OF THE DRAWINGS

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which:

Figures 6, 7:
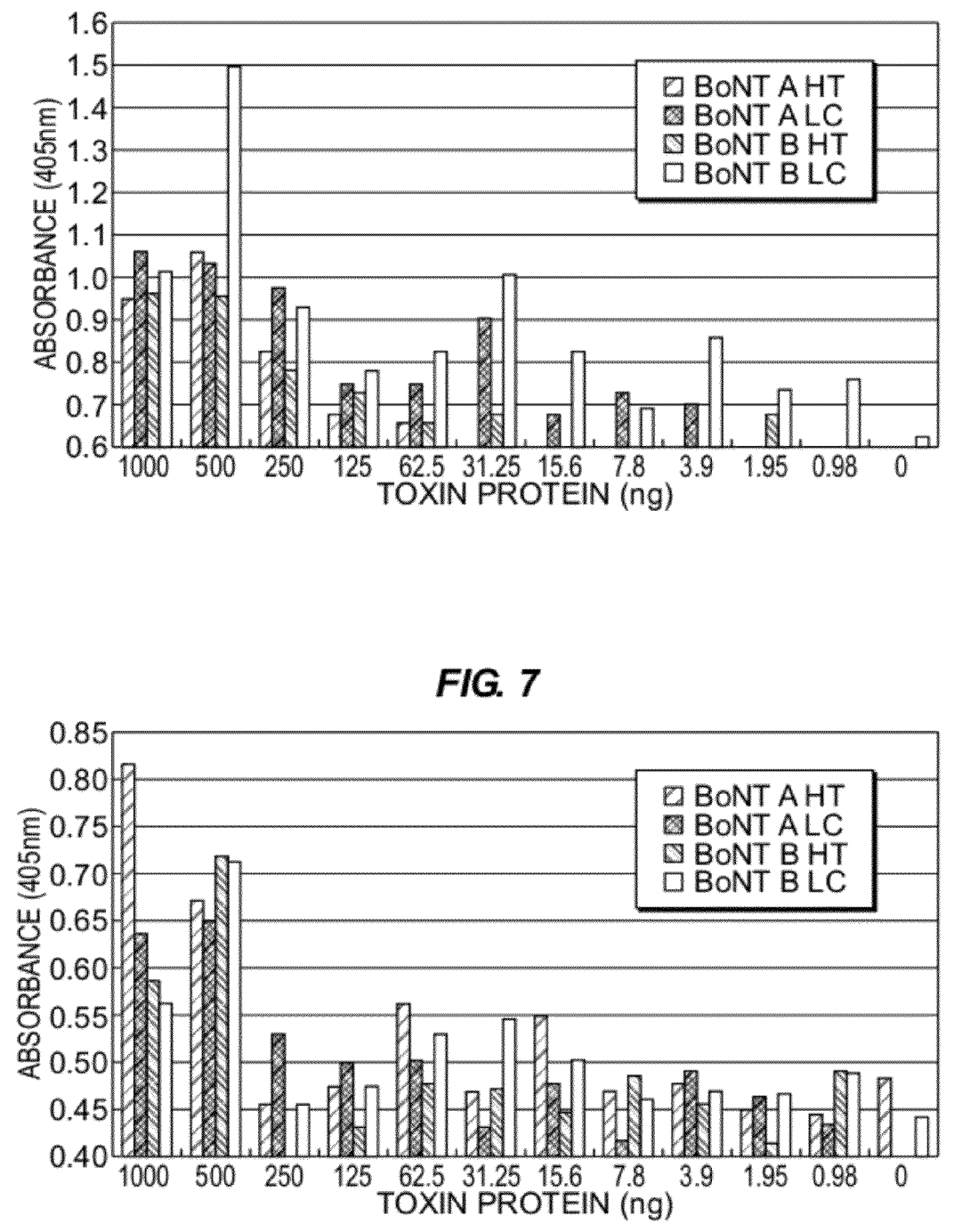

FIG. 6 shows Enzyme-Linked Aptamer Sorbent Assay (ELASA) results for an anti-botulinum A holotoxin-derived aptamer (SED ID NO 1) showing a significant level of cross-reactivity for binding of the aptamer sequence to botulinum A and B holotoxins (HT) and light chains (LC).

FIG. 7 shows Enzyme-Linked Aptamer Sorbent Assay (ELASA) results for an anti-botulinum A toxin light chain-derived aptamer (SED ID NO 2) showing a significant level of cross-reactivity for binding of the aptamer sequence to botulinum A and B holotoxins (HT) and light chains (LC).

DETAILED DESCRIPTION OF THE INVENTION

Figure 1:
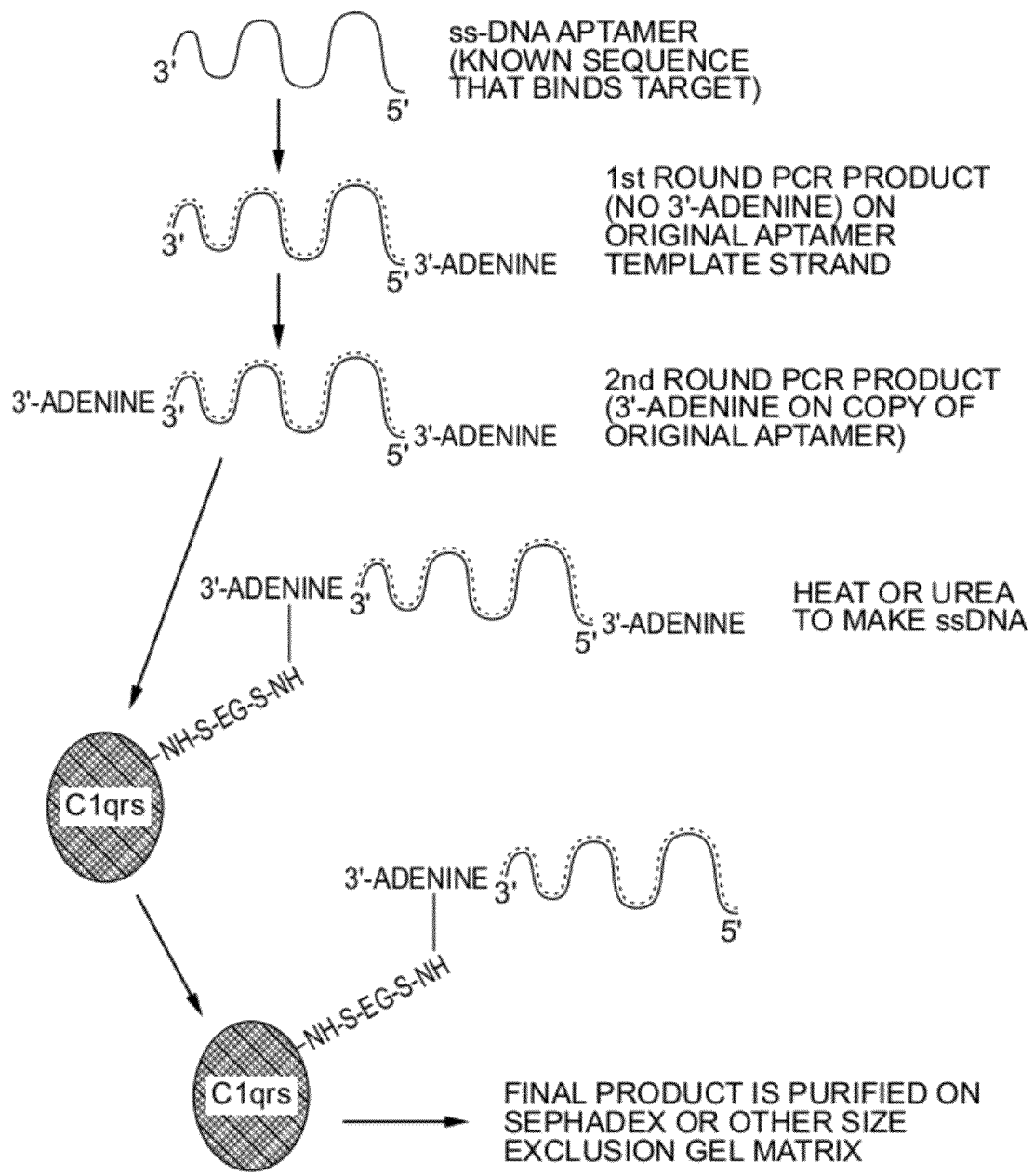
FIG. 1 shows a schematic of the process for conjugation of a known DNA aptamer sequence at its 3' end to an effector protein of choice (in this example, C1qrs to activate the complement cascade).
Figure 2:
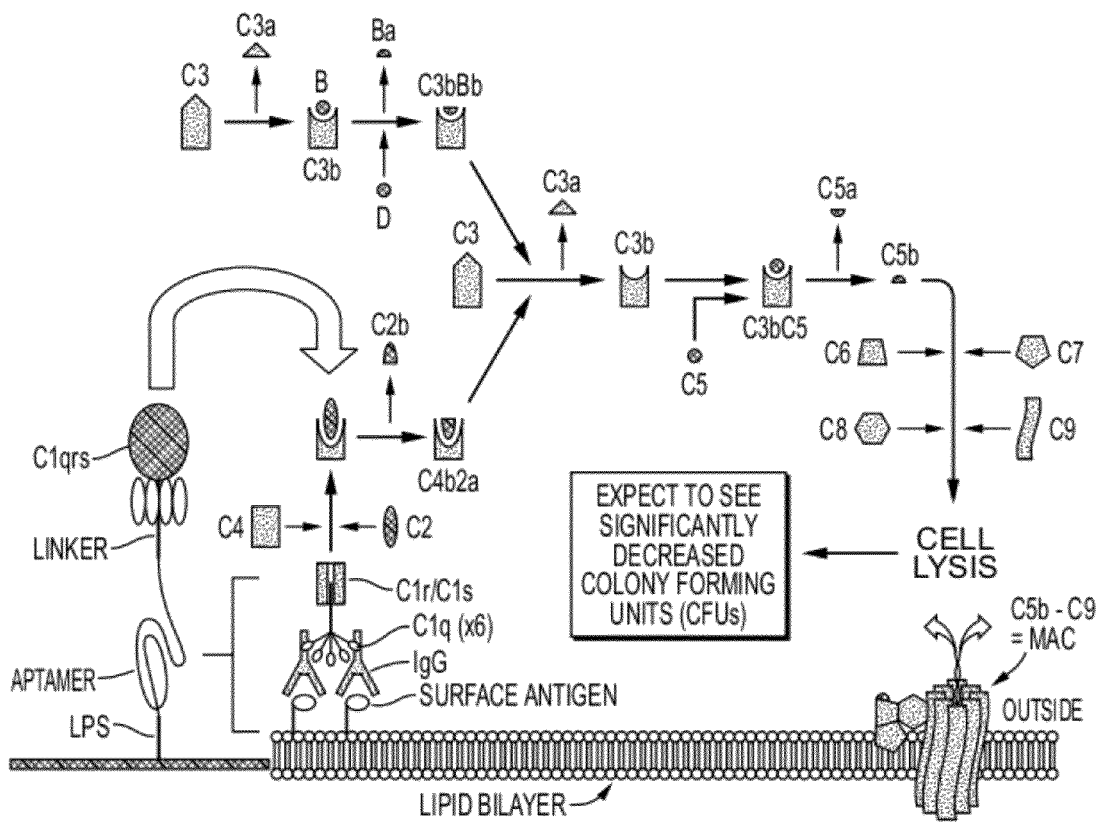
FIG. 2 shows the theoretical aptamer-3'-C1qrs conjugate bacterial killing mechanism. In the figure, IgG antibodies are replaced by the aptamer-3'-C1qrs conjugate and activate the Classical complement cascade. Lipopolysaccharide (LPS) is shown as a target surface antigen for Gram negative bacteria, but LPS could be replaced by any bacterial cell surface component that is accessible.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

As used herein, the term "aptamer" means and refers to at least one oligonucleotide that has a specific three dimensional shape and consequent biological activity. As herein defined, "aptamer" specifically includes nucleotide sequences with, in an embodiment, about 75% sequence identity (homology), or, in an embodiment, about 80% sequence identity, or, in an embodiment, about 85% sequence identity, or, in an embodiment about 90% sequence identity, or, in an embodiment, about 95% sequence identity, or, in an embodiment, about 99% sequence identity, or, in an embodiment, about 99.5% sequence identity with the aptamer of interest.

As used herein, the term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

Nucleic acid sequences cited herein are written in a 5' to 3' direction from left to right unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent, at least in part, on the nature and degree of complementarity of the sequence of bases.

As used herein, the term "nucleotide sequence" specifically includes the nucleotide sequence, its complement, derivatives, and homologs.

As used herein, "coordination complex" means and refers to a complex in chemistry usually is used to describe molecules or ensembles formed by the combination of ligands and metal ions.

The following examples are illustrative of various embodiments of the invention and are not intended to be limiting. For example, we have exemplified the invention using aptamers, but it is equally applicable to antisense, ribozymes, silencing or small interfering RNAs (siRNAs), gene therapy, and other therapeutic nucleic acids. Additionally, we have added the 3'-conjugate using the free primary amine of A, C, or G, which is a convenient means of specifically conjugating the 3' end, but other means of conjugation to the 3' end can be used. For example, the free carbonyl on G, T, C and U, can be used. Alternatively, a modified nucleotide equipped with target moieties for conjugation can be added as the 3' overhang. The diol on the 3'-ribose residue of RNA may be oxidized to result in two aldehyde groups using sodium meta-periodate and the aldehydes then can be conjugated to the amine groups on a protein using reductive amination with sodium cyanoborohydride. Nucleic acid conjugation techniques are well known in the art and need not be further detailed herein.

In various examples given herein, the bifunctional linker SULFO-EGS™ (PIERCE CHEMICAL CO.™) was used to couple the free primary amine from adenine to a protein conjugate. However, any biocompatible, nonallergenic, bifunctional linker could be used including EDP=3-[(2-aminoethyl)dithio]propionic acid; BMPH=N-[beta-maleimidopropionic acid] hydrazide; BMPS N-[beta-maleimidopropyloxy]succinimide ester; SULFO-DST= disulfosuccinimidyl tartrate; SULFO-EMCS=N-[epsilon-maleimidocaproyloxy]sulfosuccinimide ester.

Further embodiments comprise various other linkages and/or various other techniques for linking.

In an embodiment, linkage is capable of being accomplished through metal-ion mediated catalysis of relatively non-reactive primary aryl amines in adenine, cytosine and guanine by way of transition metal ions such as, but not limited to, Pt(II) and its chelates or coordination complexes as taught by Anorbe, et al., 2004.

In an alternate embodiment, linkage is capable of being accomplished through homo- and hetero-bifunctional aldehydes, such glutaraldehyde or aminoacetaldehyde, known to spontaneously attack and bind to $N^6$ amine group of adenine as taught by Gacesa and Whish, 1978; Hopwood, 1975; Rall and Lehne, 1982; Hayatsu, et al. 1982 and many others. After attachment to the primary aryl amine in the adenine, cytosine, or guanine on the 3' end of the ds-DNA, the other end of the bifunctional aldehyde can be attached to a protein by conventional means.

In an alternate embodiment, linkage is capable of being accomplished through diazotization (Sandmeyer reaction) in which the primary aryl amine is converted into a diazo ($-N=N^+$) reactive group that links to other primary amines in proteins. In an embodiment, a diazo group is created only at the primary aryl amine of the overhanging 3' adenine, cytosine or guanine bases as taught indirectly by Matsuura, et al., 2000 and Dolan, et al., 2001.

In yet an alternate embodiment, linkage is capable of being accomplished through the use of naturally occurring enzymes such as methylases or transferases known to add ligands to the primary aryl amines of adenine, cytosine, and guanine as taught by Pues, et al., 1999; Scavetta, et al., 2000; Zinoviev, et al., 1998; Harrison, et al., 1986 and Wang, et al., 2005. In an embodiment, a bifunctional linker that is a structural analog of the normal ligand substrate is attached to the primary aryl amine of adenine, cytosine, or guanine, thereby creating a covalent bond between the base on the 3'-end of the DNA and making the other end of linker available for conjugation to a protein of choice.

In various embodiments, combinations of various linkage methods are used. In an embodiment of a combination, an aldehyde on adenine $N^6$ is capable of being followed by a diazotization of the respective linker. However, any combination is possible.

Additionally, in various embodiments protein conjugates were used, because such conjugates enhance the efficacy of the invention by conferring the activity of the protein to the therapeutic nucleic acid. However, various other embodiments comprise nanotubes or other large macromolecules with desirable properties. In various embodiments, conjugates are large enough to prevent the nucleic acid-3'-conjugates from being rapidly cleared by the kidneys, while protecting the nucleic acid from degradation, without the conjugation adversely affecting the activity of either component.

In various embodiments, where the conjugate has biocidal activity, the nucleic acid-3'-conjugate can be used to selectively target and kill pathogens or cancer cells. Biocides include toxic proteins such as peptide toxin mellitin, gelonin, peroxidase, TNF-alpha, *Bacillus thuringensis* crystal (cry) proteins, and/or the like; proteins that recruit the natural cell killing mechanisms, such as C1prs, Fc, C3b, C4b, C5a, and C567; phage lysis proteins, such as the SPO1 genes 40, 50 and 51; chemicals such as polystyrenes, eugenol, thymol, trichlorocarbanalide (TCC), didecyldimethylammonium chloride (DDDMAC) and C10-16-alkyldimethyl, N-oxides (AD-MAO), Pentachlorophenol (PCP), and nanotobes containing small molecule drugs, such as antibiotics, or when used as a pore to penetrate target cells.

Other conjugates are designed merely to protect the therapeutic nucleic acid from degradation and retain its activity in the bloodstream, such as serum albumin (SA), human serum albumin (HSA), alpha1 and alpha2 globulins, beta-globulins, gamma-globulins, hemoglobin, and the like. Other conjugates can include antibodies or antibody fragments, designed to recruit other proteins or cell types to the therapeutic nucleic acid. These are particular useful in gene therapy techniques, such as suicide gene therapy or rescue gene therapy, where particular cells are to be targeted with a cytotoxic or functional gene.

Further embodiments of the present invention claim various applications. In an embodiment, embodiments of the present invention block organophosphorus nerve agent effects. Various nerve agents can be blocked by aptamer-3' conjugates to anti-methylphosphonic acid (MPA), acetylcholine, GA (tabun), sarin (GB), soman (GD), cyclosarin (GF), VX (a form of O-ethyl-S-[2(diisopropylamino)ethyl]methylphosphonothiolate), and/or the like. In an alternate embodiment, the aptamer-3' conjugates of the present invention are capable of use as anti-botulinum toxin antidotes. In further embodiments, the aptamer-3' conjugates of the present invention are capable of use in the opsonization and killing of pathogens such as anthrax and *Leishmania* parasites, as is herein illustrated. In general, aptamer-3' conjugates of the present invention are capable of conjugation to any therapeutic agent desired.

In an embodiment of the present invention, various nucleotide sequences of at least near-perfect contiguous complementarity with the nucleotide sequences of an aptamer as disclosed in SEQ ID NOS:1-31 are within the scope of the appended claims. "Near-perfect," as used herein, means the antisense strand of the nucleotide sequence is "substantially complementary to," and the sense strand of the nucleotide sequence is "substantially identical to" at least a portion of the aptamer. "Identity," as known by one of ordinary skill in the art, is the degree of sequence relatedness between nucleotide sequences as determined by matching the order and identity of nucleotides between the sequences. In one embodiment, the antisense strand of the nucleotide sequence having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

In one embodiment of the invention, an aptamer has 72 contiguous nucleotides. Accordingly, a nucleotide sequence having 85% sequence complementarity to, or at least 85% sequence identity with, the aptamer has identical nucleotides in 61 positions of the 72 nucleotide long aptamer. Eleven (11) nucleotide substitutions (i.e., 61/72=85% identity/complementarity) are included in such a phrase.

Various embodiments of the present invention have varying degrees of of sequence identity. In an embodiment, a nucleotide sequence capable of use with varying embodiments of the present invention has about 75% sequence identity with the aptamer of interest. In an alternate embodiment, a nucleotide sequence capable of use with varying embodiments of the present invention has about 80% sequence identity with the aptamer of interest. In an alternate embodiment, a nucleotide sequence capable of use with varying embodiments of the present invention has about 85% sequence identity with the aptamer of interest. In an alternate embodiment, a nucleotide sequence capable of use with varying embodiments of the present invention has about 90% sequence identity with the aptamer of interest. In an alternate embodiment, a nucleotide sequence capable of use with varying embodiments of the present invention has about 95% sequence identity with the aptamer of interest. In an alternate embodiment, a nucleotide sequence capable of use with varying embodiments of the present invention has about 99% sequence identity with the aptamer of interest. In yet an alternate embodiment, a nucleotide sequence capable of use with varying embodiments of the present invention has about 99.5% sequence identity with the aptamer of interest.

Various methods are contemplated in embodiments of the present invention.

In an embodiment, a method of the present invention comprises coupling of a PCR product having a 3' adenine overhang to a protein, peptide, or other macromolecule which is already coupled to thymine or uridine with a spacer or linker arm of one or more nucleotides followed by the formation of a contiguous phosphate backbone via the addition of DNA ligase.

In an alternate embodiment, a method of the present invention comprises a method of treating a pathogenic infection, comprising the steps of: administering an aptamer-3'-biocide conjugate to a patient with a pathogenic infection in an amount sufficient to prevent a target pathogen from reproducing; wherein the aptamer binds specifically to said target pathogen and is coupled via a bifunctional linker to a biocide conjugate that prevents said target pathogen from reproducing.

In an alternate embodiment, a method of the present invention comprises a method of killing a cancer cell in vivo, comprising the steps of: administering an aptamer-3'-biocide conjugate to a patient with an cancer cell in an amount sufficient to prevent said cancer cell from reproducing; wherein the aptamer binds specifically to said cancer cell and is coupled via a bifunctional linker to a biocide conjugate that prevents said cancer cell from reproducing.

In an alternate embodiment, a method of the present invention comprises a method of preparing a DNA-3'-conjugate comprising: preparing a ds-DNA with a 3' overhang of adenine (A), cytosine (C), or guanine (G) deoxynucleotides on said ss-DNA strand of interest; coupling the primary amine of the 3' overhang to a protein conjugate via a Metal ion, metal ion chelate, or coordination complex catalysis for the attachment of at least one linker; and separating said ds DNA into ss DNA and ss-DNA-3'-conjugate and purifying said ss-DNA-3'-conjugate for therapeutic use, or optionally purifying said ds-DNA-3'-conjugate for therapeutic use.

In an alternate embodiment, a method of the present invention comprises a method of preparing a DNA-3'-conjugate comprising: a) preparing a ds-DNA with a 3' overhang of adenine (A), cytosine (C), or guanine (G) deoxynucleotides on said ss-DNA strand of interest; b) coupling the primary amine of the 3' overhang to a protein conjugate by enzymatic attachment of reactive linkers to the primary amines of adenine, cytosine, and/or guanine using methylases, alkyl transferases, and/or modified enzymes to said protein conjugate and said ds-DNA for the attachment of at least one linker; and c) separating said ds DNA into ss DNA and ss-DNA-3'-conjugate and purifying said ss-DNA-3'-conjugate for therapeutic use, or optionally d) purifying said ds-DNA-3'-conjugate for therapeutic use.

In an alternate embodiment, a method of the present invention comprises a 3'-capped or otherwise nuclease-resistant aptamer to bind and block the activity of quorum sensing molecules such as acyl-homoserine lactone (AHL) autoinducers which communicate between bacteria in vivo and in topical or deep skin and soft tissue wounds to trigger proliferation, adherence, toxin production, other virulence factor production, and biofilm formation.

In an alternate embodiment, a method of the present invention comprises a use of an antibacterial apamter-3'-C1qrs conjugates in combination with other serum complement proteins in a topical skin cream to kill antibiotic-resistant bacteria such as methicillin-resistant *Staphylococcus aureus* (MRSA).

In an alternate embodiment, a method of the present invention comprises a use of an aptamer-3'-C1qrs conjugates in combination with other serum complement proteins in a topical skin cream to kill acneiform bacteria and treat acne.

In an alternate embodiment, a method of the present invention comprises a use of a 3'-capped of otherwise nuclease-resistant anti-dihydrotestosterone (DHT) and/or 3'-capped anti-5-alpha reductase aptamers in a topic skin cream, foam, or liquid spray to treat male pattern baldness.

In an alternate embodiment, a method of the present invention comprises a use of a 3'-capped or otherwise nuclease-resistant anti-inflammatory or anti-fungal aptamers to treat various forms of dermatitis such as eczema, seborrhea, and psoriasis.

In an alternate embodiment, a method of the present invention comprises a use of an antibacterial aptamer-3'-C1qrs conjugates in combination with other serum complement proteins in a liquid or spray to treat sinus, eye, and ear infections.

In an alternate embodiment, a method of the present invention comprises a use of an anti-inflammatory 3'-capped or otherwise nuclease-resistant aptamers in liquid spray form for intranasal administration to treat allergy symptoms.

In an alternate embodiment, a method of the present invention comprises a 3'-protein capped or otherwise nuclease-resistant anti-cytokine (e.g., transforming growth factor-beta (TGF-beta) and anti-tumor necrosis factor-alpha (TNF-alpha)) aptamers in topical skin creams or ointments to bind and neutralize cytokines in wounds to lessen scar formation during wound healing.

In an alternate embodiment, a method of the present invention comprises a 3'-capped or otherwise nuclease-resistant aptamers to stimulate vascular endothelial growth factor (VEGF) to promote angiogenesis during wound healing.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

Example 1

Nucleic Acid-3'-Protein Conjugation

Two prime (2') modifications of nucleotides in RNA aptamers have been reported to work well for nuclease resistance (Bell et al., 1999 and Ulrich et al., 2002) against certain specific bacterial nucleases and against serum nucleases. Some researchers claim that DNA aptamers can be protected by 2'-Fluoro-deoxynucleotide (dNTP) incorporation (Ono et al., 1997). However, there is not much definitive data on this topic in the literature. Further, it is difficult to incorporate 2'F-dNTPs into DNA by PCR (Ono et al., 1997) or other means as most DNA polymerases either will not incorporate 2'F-dNTPs (i.e., reject them as substrates or they are poorly incorporated) or the 2'-F-dNTPs are excised by the polymerase's editing function.

An alternative method for conferring resistance to serum nucleases is capping of the DNA termini, especially the 3' end as shown by Dougan et al. (2000). Dougan capped aptamers with the small molecule biotin and successfully preserved the aptamers in serum. However, we theorized that a larger peptide or protein could be conjugated to the 3' end of the aptamer with the added benefits of increasing aptamer retention in the blood (i.e., decreasing clearance by the kidneys, because the low molecular weight aptamer is attached to a large protein that cannot be filtered by the kidneys). In addition, a protein conjugate would provide the benefit of adding the functionality of the protein conjugate to the aptamer. The latter advantage can then be used for adding a wide variety of functions such as biocidal activity, enzymatic activity, enhancing phagocytosis (opsonization), cell recruitment or cell activation, or serum stability.

The goal of the process shown schematically in FIG. 1 was to terminate the aptamer in a deoxynucleotide containing a free amine group at the 3' end to enable covalent coupling to the protein conjugate. In an embodiment, the aptamer may or may not have a free 3' amine group originally, but conjugation of a single-stranded aptamer would surely lead to a family of conjugates at different positions on the aptamer and no guarantee of serum nuclease resistance, or retention of aptamer activity. Hence, the aptamer is subjected to at least one round of the polymerase chain reaction (PCR) to create a complementary strand (dotted line) and a 3'-adenine (A) overhang that has a free amine moiety.

In various embodiments, the 3'-A overhang is on the complementary strand, not on the desired aptamer strand. Therefore at least one more round of PCR is required to place the 3'-A overhang on the original template strand (solid line) and enable conjugation to the protein conjugate by means of a common bifunctional linker such as SULFO-EGS™ (ethylene glycol-bis (sulfosuccinimidylsuccinate)). However, specifically included with this disclosure are aptamers wherein the 3'-A overhang is on the desired aptamer strand, not on the complementary strand, thereby only requiring one round of PCR.

Once the aptamer is conjugated to a given protein at its 3' end, the double strand is melted by means of heating. The conjugate is heated to a temperature and/or for a period of time that will not denature the protein. In various other embodiments, a mild chemical treatment such as low concentrations of urea, which could again denature the protein if the concentration is too high. Other means of separating ds-DNA include the use of biological tools, such as SSB (Single-stranded DNA Binding Protein) or helicases.

Finally, the single-stranded aptamers and the aptamer-3'-protein conjugates can be separated by a variety of physical means such as size exclusion gel chromatography on materials such as Sephadex, Sepharose, Superdex, density gradient centrifugation, or preparative electrophoresis, etc. The aptamer-3'-conjugate can also be separated by affinity chromatography using an antibody against the protein conjugate, and this system can be coupled with mild denaturation, thus allowing purification and separation in a combined step.

Bruno (1997) and Bruno and Kiel (2002) as well as Murphy et al. (2003) have described a method for immobilizing target molecules onto magnetic microbeads (MBs) and using these target-MBs to magnetically separate out aptamers from a randomized oligonucleotide library which bind the target with high affinity. Then using standard SELEX techniques (Bruno and Kiel 2002), a family of aptamers can be selected that will bind the target with high affinity and can be conjugated at their 3'ends by way of the process shown in FIG. 1.

Example 2

Antibiotic Aptamer-3'-C1QRS

Sulfo-EGS was dissolved at 10 mg/mL in sterile PBS and 132 μL of this stock solution added to 0.1 mg of human C1qrs protein (molecular weight of 750 kD). This ratio provided the 20-fold molar excess of Sulfo-EGS recommended for Sulfo-EGS conjugations.

One hundred μL (approximately 33 μg) of SELEX round 5 or greater DNA aptamers in their cold (double-stranded) form was added to the solution. The reactants were allowed to stand at room temperature (RT) for 1 hour and were then added to a PHARMACIA™ PD-10 desalting column (SEPHADEX™ G-25) equilibrated with several void volumes of sterile PBS. Twelve to fifteen 1 mL fractions were eluted in PBS and collected as individual fractions. Absorbance readings were taken for all fractions at 260 nm and 280 nm. In addition, 5 μL of each fraction was added to 5 μL of native polyacrylamide gel electrophoresis (PAGE) loading buffer and run on 8-10% polyacrylamide gels that were fixed and silver stained to verify successful conjugation by gel shift analysis.

The following steps were performed for *E. coli* O111:K58 (B4):H- (ATCC No. 33780) killing experiments. Twenty tryptic soy agar (TSA) petri plates were warmed to RT and labeled to represent four groups of five plates each. The five plates cover arbitrary E. coli ten-fold dilutions from $10^{-4}$ to $10^{-8}$ where the aptamer-C1qrs conjugates "antibiotic" effect was anticipated. One loopful of freshly cultured *E. coli* O111: K58(B4):H- (i.e., grown overnight at 35° C. on TSA agar) was added to 1 mL of Gelatin Veronal Buffer (GVB; SIGMA-ALDRICH CO.™, St. Louis, Mo.) at RT. Clumps were broken up by use of a 5 mL syringe and 20 gauge needle that was used to vigorously eject the bacterial sample ten times to achieve a uniform single cell suspension, as confirmed by phase-contrast microscopy at 400× magnification.

This stock bacterial suspension was used to make eight ten-fold dilutions in sterile polypropylene tubes. Both the stock bacterial suspension and nascent dilution were thoroughly mixed throughout the experiments to ensure random sampling. Fifty μL of each bacterial dilution was added to four other polypropylene microfuge tubes (representing the four treatment groups for each specified dilution of interest).

Ten μL of human serum complement proteins (SIGMA-ALDRICH™ #S-1764) diluted 1:500 (to avoid activation of the alternate complement pathway by LPS) in GVB was added to each tube in Groups 1 and 2.

One hundred μL of the aptamer-3'-C1qrs conjugate was added to five separate PCR tubes, and all were heated at 80° C. in the thermal cycler block for 5 minutes to make the anti-LPS aptamer portion of the conjugate single-stranded (Tm of the 60mer was 78.5° C.). This temperature and duration did not appear to cause damage to the C1qrs part of the conjugate, because it still appeared to initiate bacterial killing, as shown below.

Fifty μL of the hot aptamer-C1qrs conjugate was added to Groups 1 and 4 of each killing experiment (50 μL×10 tubes=500 μL). Total volume of all tubes was equalized to 110 μL by addition of GVB as appropriate. Tubes were capped, shaken ten times, and incubated at 35° C. for 2 hours.

The tubes were decanted onto the TSA plates and the contents spread. Plates were placed face up at RT for 30 minutes and then inverted and incubated overnight at 35° C. The following day, plate counts were obtained and all plates were photographed.

It is well known that LPS from *E. coli* and other Gram negative bacteria can activate the complement cascade by the Alternate pathway. To eliminate or minimize the Alternate pathway of complement activation, a series of dilutions containing only human serum complement protein (HSCP) were added to the test bacteria to determine the lowest concentration (i.e., highest dilution) of HSCPs that did not kill significant numbers of *E. coli* bacteria by the Alternate pathway after a two hour incubation at 35° C. The results of the HSCP dilution experiment are given in Table 1 and indicate that between a 1:800 to 1:500 dilution of the HSCPs was appropriate for use in the later killing experiments, since that is where the killing effect of HSCP itself becomes apparent (i.e., significantly fewer than 300 colonies were seen per plate).

TABLE 1

Colony Counts of *E. coli* O111:B4 as a Function of HSCP Dilution
Colony Forming Units (cfu)

| HSCP Dilution | Trial 1 | Trial 2 |
|---|---|---|
| 1:10,000 | >300 | >300 |
| 1:1,000 | 287 | 283 |
| 1:800 | 241 | 238 |
| 1:500 | 187 | 172 |
| 1:400 | 98 | 90 |
| 1:200 | 57 | 63 |
| 1:100 | 18 | 21 |

Note:
An arbitrary $10^{-4}$ dilution of *E. coli* was used. Gray highlights indicate that at those dilutions there was sufficient complement to begin activating the alternate pathway of cell killing.

The aptamer-3'-C1qrs-mediated killing experiments contained four treatment groups as follows:

Group 1: Full Test Group—Contained 50 μL of the bacterial dilution plus 50 μL of anti-LPS aptamer-C1qrs conjugate and 10 μL of 1:500 dilution of HSCPs per tube.

Group 2: Control for Alternate Pathway Activation—Contained 50 μL of bacterial dilution and 10 μL of 1:500 dilution of HSCPs plus 50 μL GVB per tube.

Group 3: Bacterial Growth Control—No chemical additives. This group indicates baseline growth levels of the bacteria. The group contained only 50 μL bacterial dilution and 60 μL of GVB per tube.

Group 4: Aptamer-C1qrs Conjugate Control—Contained only 50 μL of bacterial suspension plus 50 μL of aptamer-C1qrs conjugate and 10 μL of GVB (no HSCPs added, therefore the remainder of the complement cascade should not be present).

In the three aptamer-C1qrs bacterial killing experiments (Table 2), it became clear that, at certain higher dilutions, Groups 1 and 4 consistently showed fewer colonies than Groups 2 and 3. If the classical pathway of complement activation was being invoked by the anti-LPS aptamer-C1qrs conjugate, then one would predict a significantly lower number of colonies in Group 1. However, the lower number of colonies in Group 4 (conjugate only group) is somewhat perplexing. One possible explanation of the lowered colony numbers in Group 4 is that traces or residues of the other complement proteins (HSCPs) are present in the aptamer-C1qrs conjugate preparation and synergize with the conjugate to bring about elevated levels of bacterial killing. If that is not the case, then the aptamer-C1qrs conjugate may be able to kill bacteria by an unknown alternate mechanism that does not involve invoking the action of the complement cascade.

TABLE 2

Colony Counts from Three *E. coli*
Aptamer-C1qrs Killing Experiments

| | Dilution | | | | |
|---|---|---|---|---|---|
| Group | 10e-4 | 10e-5 | 10e-6 | 10e-7 | 10e-8 |
| Experiment 1 | | | | | |
| 1 | TNTC | TNTC | 1 | 0 | 1 |
| 2 | TNTC | TNTC | 267 | 16 | 3 |
| 3 | TNTC | TNTC | 265 | 15 | 2 |
| 4 | TNTC | TNTC | 132 | 5 | 1 |

TABLE 2-continued

Colony Counts from Three E. coli Aptamer-C1qrs Killing Experiments

| Group | Dilution | | | | |
|---|---|---|---|---|---|
| | 10e-4 | 10e-5 | 10e-6 | 10e-7 | 10e-8 |
| Experiment 2 | | | | | |
| 1 | TNTC | TNTC | 141 | 13 | 0 |
| 2 | TNTC | TNTC | TNTC | TNTC | 207 |
| 3 | TNTC | TNTC | TNTC | TNTC | 216 |
| 4 | TNTC | TNTC | TNTC | TNTC | 67 |
| Experiment 3 | | | | | |
| 1 | TNTC | 199 | 34 | 4 | 0 |
| 2 | TNTC | TNTC | 167 | 55 | 2 |
| 3 | TNTC | TNTC | 155 | 74 | 3 |
| 4 | TNTC | 212 | 32 | 7 | 0 |

Note:
TNTC; Too Numerous to Count

Example 3

Antitoxin Aptamer-3'-HSA

Figure 3:
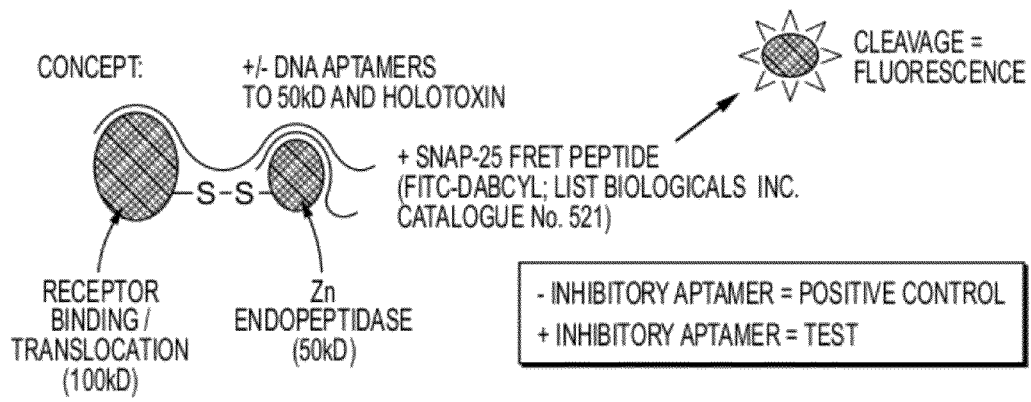
FIG. 3 illustrates how an aptamer can be used to inhibit or inactivate a toxin, such a botulinum toxin. The aptamer-3'-protein conjugate is not shown in this figure, but human serum albumin would be a good candidate for such conjugation to ensure no allergic reaction in human patients. The figure shows botulinum toxin as an example and illustrates binding and inhibition of the holotoxin and the 50 kiloDalton zinc endopeptidase subunit, which is enzymatically active on the SNAP25 peptide in neurons and is used as the basis for a fluorescence resonance energy transfer (FRET) assay known as the SNAPtide™ assay.

FIG. 3 illustrates the general concept of aptamer (or aptamer-3'-protein conjugate) binding to toxins to inhibit or inactivate the toxin. If the toxin is a small molecule that is inherently toxic to biological systems, then the binding of target-specific developed aptamers should ameliorate or eliminate toxicity by stoichiometrically wrapping around the toxin to disallow it from interacting within a biological system. If the toxin is an enzyme, then binding of a specific aptamer or aptamer-3'-protein (albumin) conjugate to the active site should diminish or cease enzymatic activity.

Figure 4A:
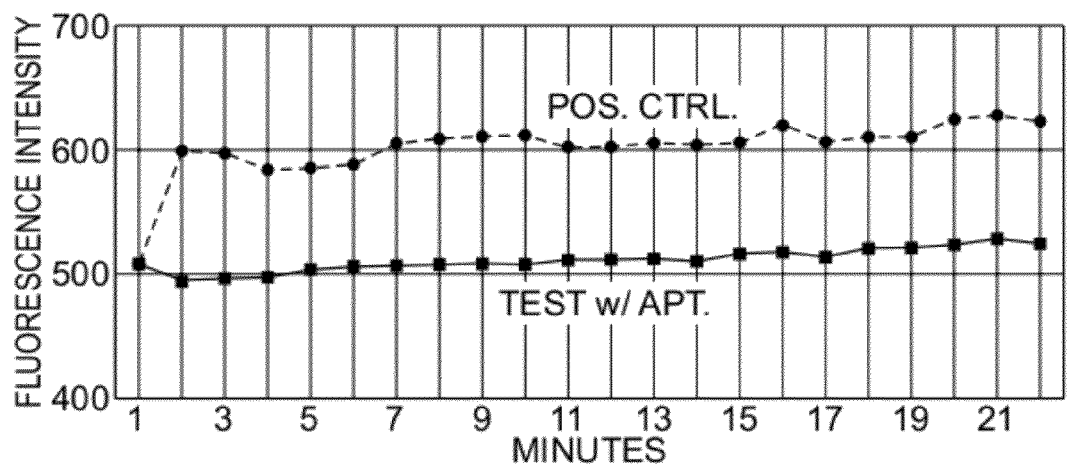
FIG. 4 shows clear inhibition (decreased light levels) of botulinum toxin serotype A (BoNT A) by DNA aptamers developed against BoNT A holotoxin (panel A) and the 50 kD zinc endopeptidase subunit (panel B) using the SNAPtide™ FRET assay. In the SNAPtide™ FRET assay, the greater the fluorescence intensity, the greater the BoNT A activity, because more SNAP 25 FRET substrate is cleaved.
Figure 4B:
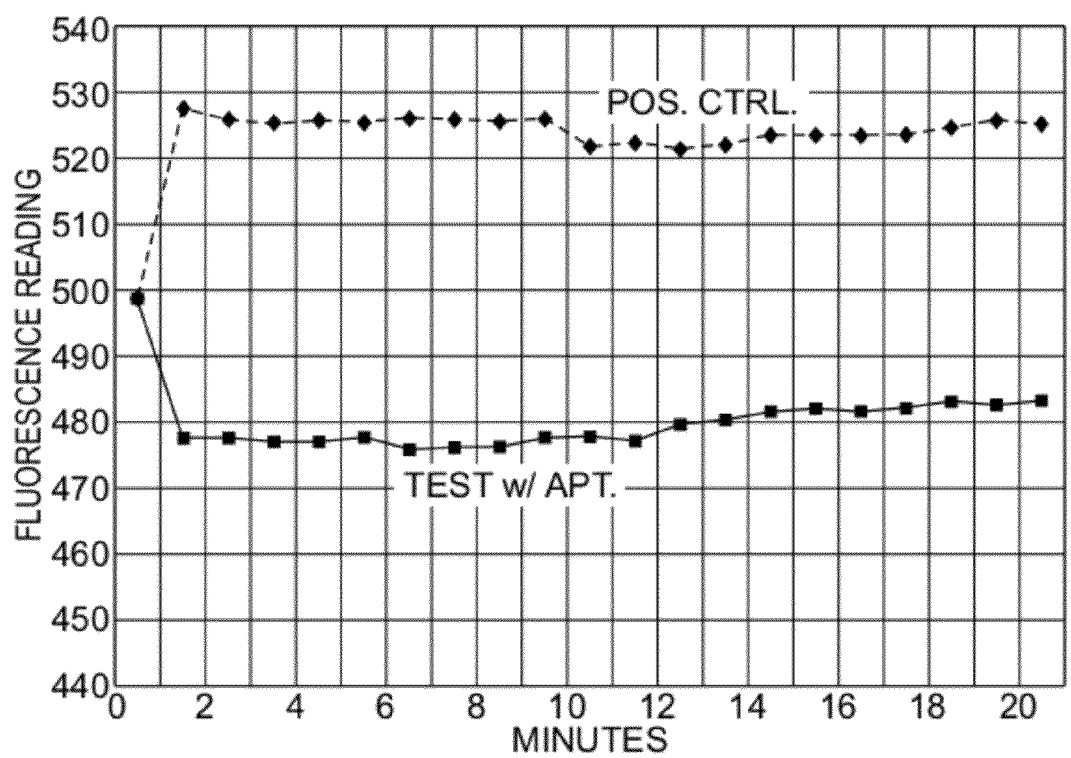
Figure 5:
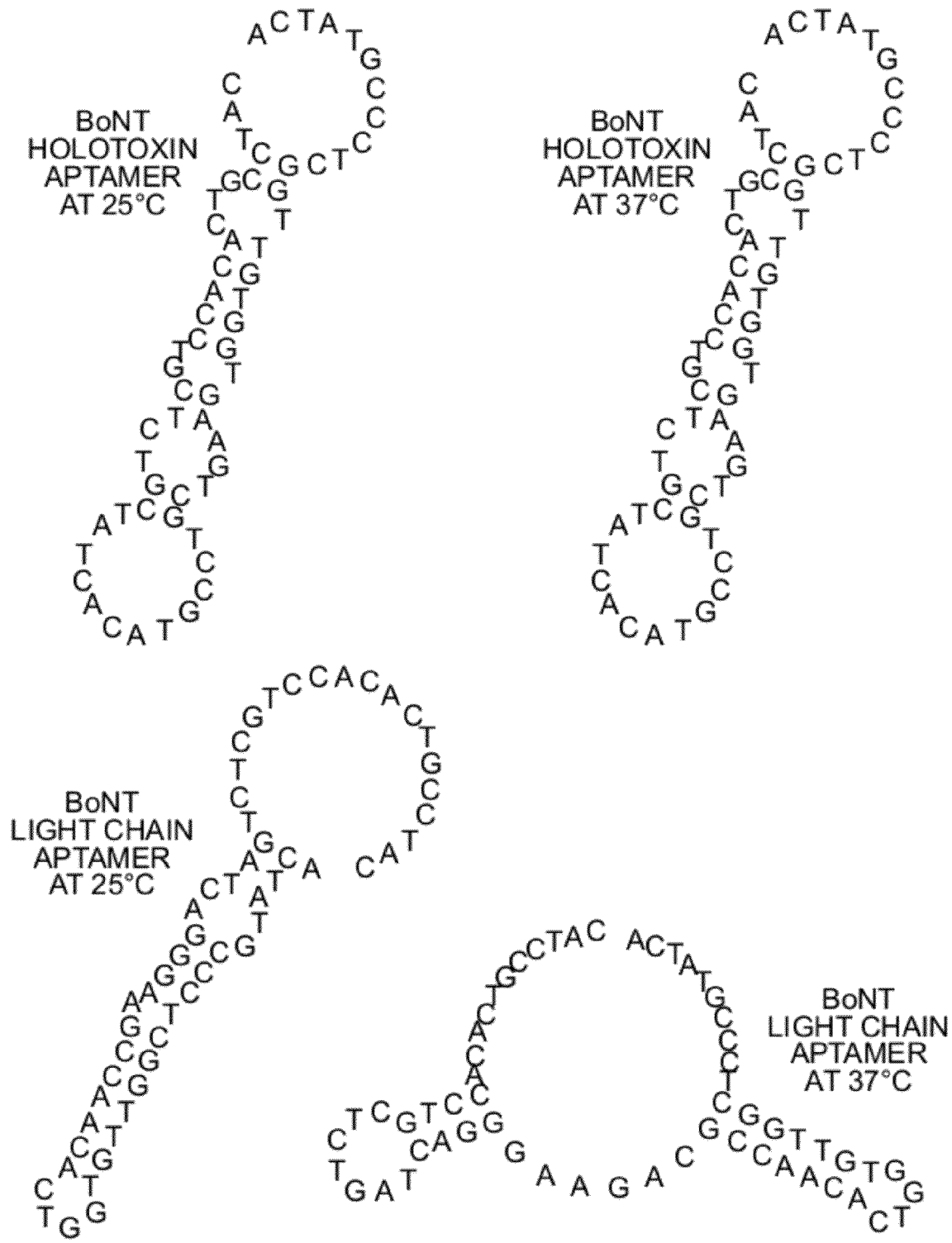
FIG. 5 shows Secondary stem-loop structures of the various DNA aptamers developed against botulinum neurotoxin (BoNT) serotype A holotoxin (SEQ ID NO. 1) and its enzymatic light chain (SEQ ID NO. 2). Structures were derived from Vienna RNA free energy minimization software using DNA parameters and room temperature input.
Figure 8:
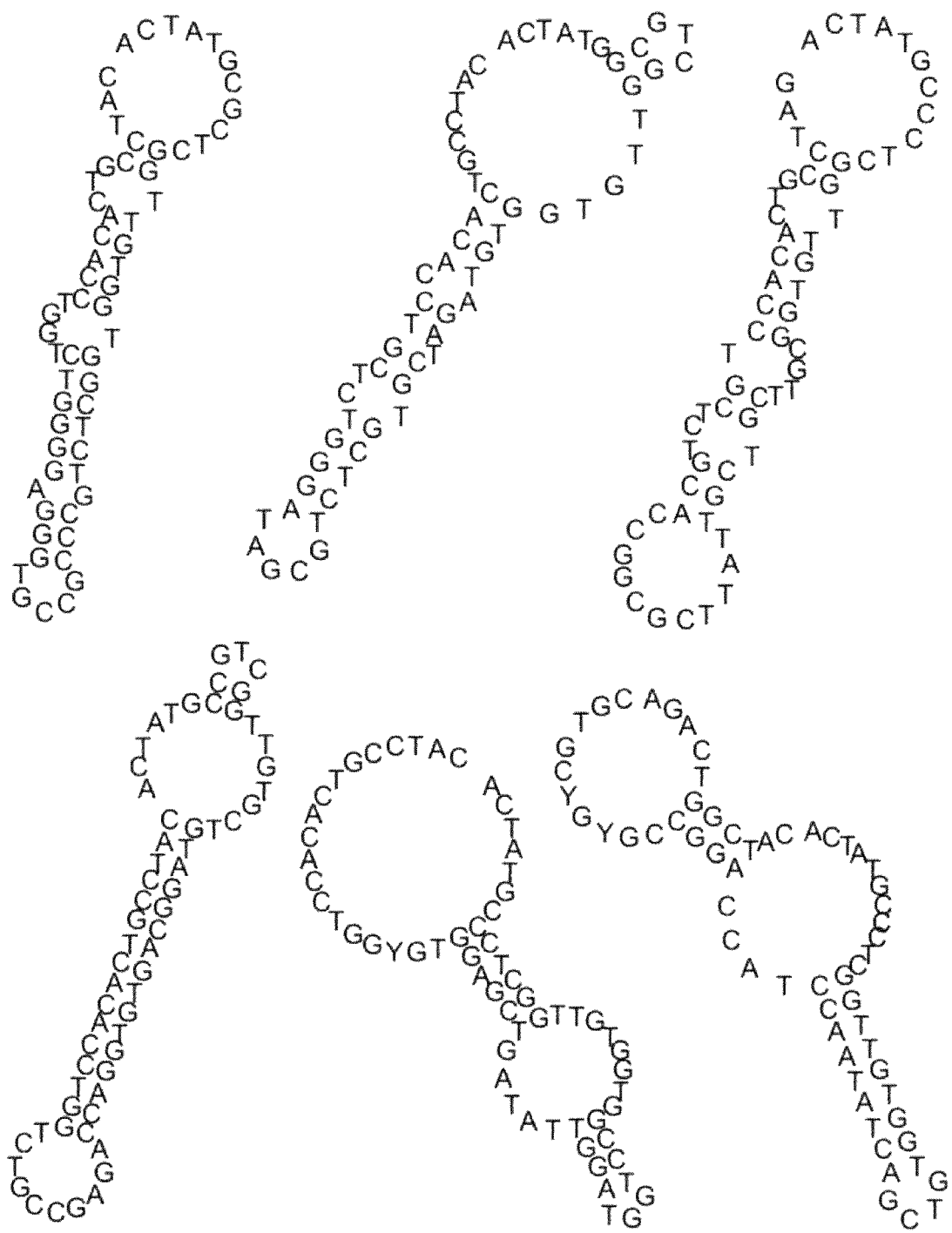
FIG. 8 shows Secondary stem-loop structures of DNA aptamer sequences (SEQ ID NOS. 3-8) known to bind *Campylobacter jejuni* surface epitopes. Structures were derived from Vienna RNA free energy minimization software using DNA parameters and room temperature input.
Figure 9:
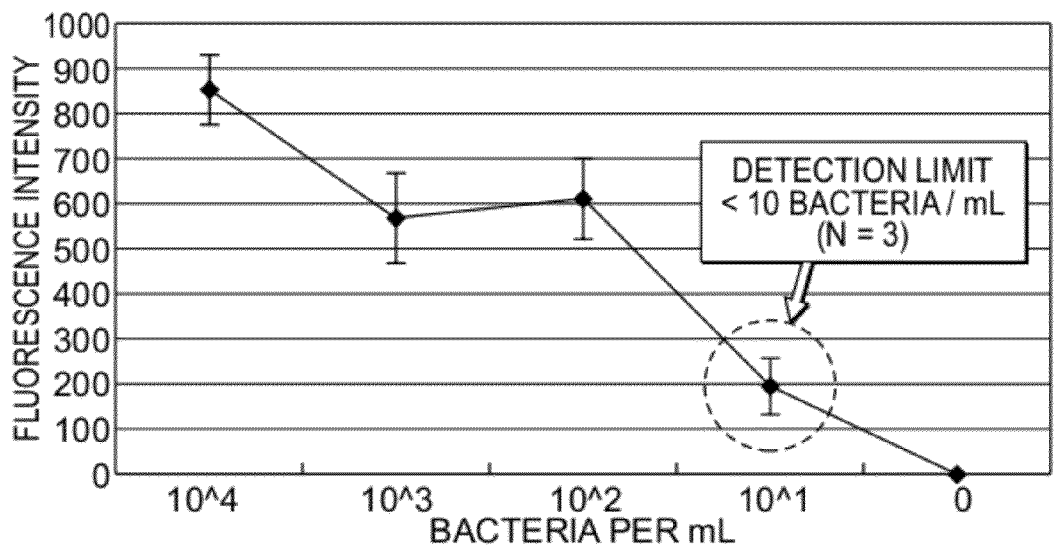
FIG. 9 shows Fluorescence binding curve for the best combination of DNA aptamer sequences used to detect *Campylobacter jejuni* bacteria to a level of 10 bacteria per milliliter using an immunomagnetic bead sandwich assay format referred to as the Magnetically Assisted Test Strip or "MATS." In the sandwich assay the C2 aptamer (SEQ ID NO 4) was covalently coupled to tosyl-magnetic microbeads and used to capture *C. jejuni* bacteria, followed by detection of bacterial capture with the C3 aptamer which was covalently linked to a red quantum dot (reported aptamer C3; SEQ ID NO. 5). Data points along the curve represent means of 3 independent readings and errors bars represent one standard deviation of the mean value.
Figure 10:
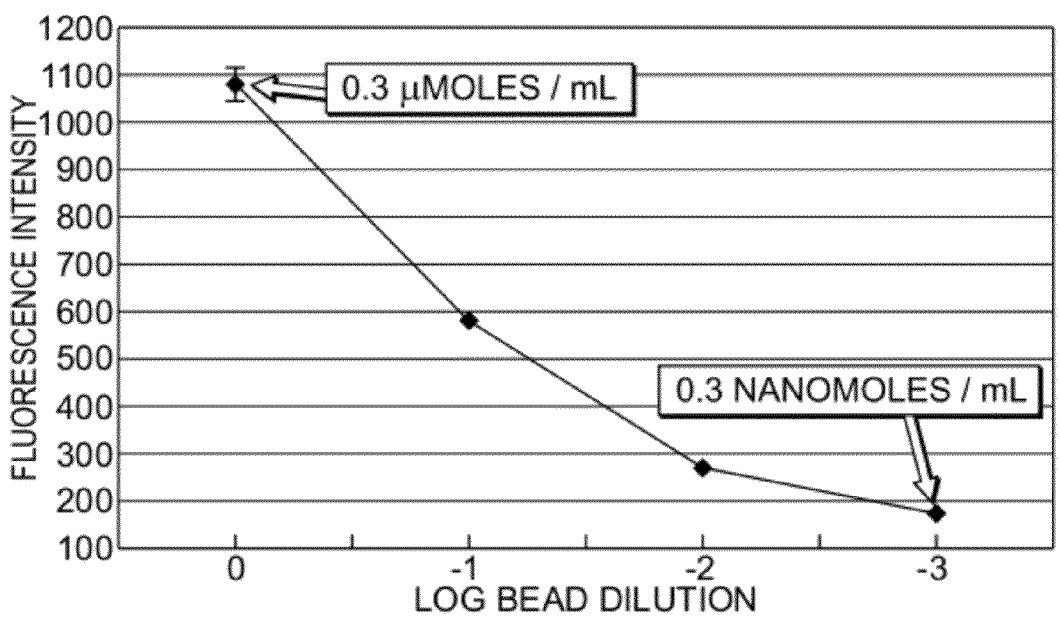
FIG. 10 shows Fluorescence binding curve for detection of methylphosphonic acid (MPA) bound as amino-MPA linked to tosyl-magnetic microbeads and then reacted with the anti-MPA DNA aptamer (SEQ ID NO. 31) having a 5'-fluorescein added to enable detection. Data points along the curve represent means of 3 independent readings and errors bars represent one standard deviation of the mean value.

One example of DNA aptamer-mediated enzymatic toxin inhibition can be seen in the binding of specific botulinum A toxin (BoNT A) aptamers to BoNT A, thereby inhibiting the toxin's ability to cleave its SNAP 25 peptide substrate. Using a specific SNAP 25 FRET assay known as the SNAPtide™ assay, aptamers developed against both the holotoxin and the 50 kd) zinc endopeptidase subunit of BoNT A showed evidence of significant toxin inhibition as seen in FIG. 4. Thus, it is shown that conjugation to a protein did not decrease either the aptamer or the protein conjugate's activity.

The SNAPtide™ assay procedure and buffer formulations are given here. 100 mL of Buffers A and B were made in nuclease-free sterile water according to Table 3 below. The pH was adjusted to 8.0 with strong base or acid, as needed, and the solutions filter sterilized and stored in a refrigerator, but warmed to RT before use.

A SNAPtide™ vial (fluorescein/dabcyl labeled peptide; LIST BIOL. LABS,™ No. 521) was reconstituted in 80 μL of DMSO to a stock concentration of 2.5 mM. 10 μL of Bot A (10 μg/mL) was preincubated in 190 μL of Buffer A (see composition below) at 37° C. for 30 minutes to activate the toxin.

10 μL of round 5 anti-BoNT A aptamers was added to 90 μL of Buffer B, mixed and preheated to 95° C. for at least 5 minutes in a closed Eppendorf tube under a vented chemical or biological hood.

Hot aptamer solution (100 μL) was added to 100 μL of activated BoNT A in an Eppendorf tube and allowed to bind at 37° C. for 15 minutes. This tube was labeled "Test." Similarly, 100 μL of Buffer B was added to 100 μL of activated BoNT A labeled "Control" and incubated t 37° C. for 10 minutes.

3 μL of stock SNAPtide™ (SNAP 25 FRET peptide fragment) were added to both tubes along with 2.7 mL of Buffer B. The contents of the tubes (3 mL each) were transferred to separate 10 mm methacrylate cuvettes and readings taken by spectrofluorometer with excitation at 490 nm and emission at >520 nm for the next 30 minutes in 1 to 2 minute intervals.

TABLE 3

Buffer Recipes for the SNAPtide™ Assay Components

| Buffer | 1M HEPES | ZnCl$_2$ | 1M DTT | BSA | Tween 20 | Nuclease Free Water* |
|---|---|---|---|---|---|---|
| A | 2 mL | 4 mg | 500 μL | 100 mg | 0 | 97.5 mL |
| B | 2 mL | 4 mg | 125 μL | 0 | 100 μL | 97.775 mL |

Abbreviations: DTT; dithiothreitol, BSA; bovine serum albumin.

Example 4

Opsonin Aptamer-3'-Fc or Aptamer-3'-C3b Conjugate

If aptamers are conjugated at their 3' end to the Fc fragment of IgG antibodies or the C3b component of complement, they could conceivably be used to opsonize encapsulated bacteria. To test this contention, tosyl-MBs (Dynal Corp.) were conjugated to poly-D-glutamic acid (PDGA) as previously described by Bruno and Kiel (2002). PDGA is the major component of the capsule of *Bacillus anthracis* (anthrax) pathogenic strains, which enables the vegetative cells to escape phagocytosis. PDGA-conjugated MBs were used to emulate vegetative anthrax bacteria and determine if aptamer-3'-Fc conjugates could enhance the phagocytosis of PDGA-MBs and by inference, opsonize encapsulated bacteria. The following describes the protocols used in these experiments.

RAW264.7 murine macrophages were split by scraping and add $10^5$ cells into each well of a sterile six-well culture plate using fresh RPMI-1640 cell culture medium plus 10% fetal bovine serum (FBS). In practice, 1 mL of cell suspension was used with 4 mL of fresh RPMI-1640 plus 10% FBS. The plate sat overnight to allow the cells to attach.

Five different tubes were labeled per Table 4 as follows (all volumes in μL):

TABLE 4

| Tube Contents | | | | | |
|---|---|---|---|---|---|
| Rd 5 Apt* | — | — | 20 | — | — |
| Fc-Apt* | — | — | — | 20 | 20 |
| 2XBB | 50 | 50 | 30 | 30 | 30 |
| Final Volume | 60 | 60 | 60 | 60 | 60 |

*Note:
Round 5 aptamer heated at 95° C. for 5 minutes prior to adding to tube; Apt. = aptamer, Fc-Apt conjugate heated at 65° C. for 5 minutes prior to adding to tube. Heating is performed to ensure single-strandedness of the aptamers before they bind PDGA. 2XBB = 2X aptamer binding buffer (Bruno and Kiel, 2002).

Each tube was incubated for 30 minutes at RT to allow binding of any aptamers or aptamer-Fc conjugates with PDGA-MBs or other targets to occur Tube contents were loaded to the appropriate wells of a 6-well plate, and incubated at 37° C. and 5% $CO_2$ and then counted at 1, 2, and 24 hours using an inverted microscope.

Data were evaluated using a "phagocytic index" parameter. The formula used for the phagocytic index according to Welkos et al., 2001 was:

Phagocytic Index=Mean number of MBs/cell $X$ % of cells with at least one MB

Table 5 summarizes the raw data from the opsonization studies, as well as the phagocytic indices, which were derived from the above equation using the raw data. The controls that appeared to show enhanced phagocytosis may be due to some nonspecific binding of the aptamers to other targets or the innate ability of macrophages to recognize certain types of foreign matter (MBs or coated MBs). It also appears from Table 5 that there was some dose-dependence to the Fc-aptamer enhancement because in the first experiment the percentage of cells showing phagocytosis jumped from 74.67% to 96% with an increased level of Fc-aptamer conjugate (see highlighted data in Table 5).

TABLE 5

Raw Data and Phagocytic Indices for Aptamer-Fc Conjugate Studies

| | # of cells counted | # w/o MB association | # of MB | Mean # of MB per Cell | % cell w/MB | Phagocytic Index |
|---|---|---|---|---|---|---|
| Macrophage Test No. 1: 24 hr. Count | | | | | | |
| Well | | | | | | |
| Blank (2XBB) | 300 | 300 | 0 | 0 | 0.00% | 0.00 |
| 5 uL Tosyl-MBs | 300 | 138 | 416 | 1.39 | 54.00% | 0.75 |
| 50 uL PDGA-MB + FcApt | 300 | 12 | 586 | 1.95 | 96.00% | 1.88 |
| 5 uL PDGA + FcApt | 300 | 76 | 402 | 1.34 | 74.67% | 1.00 |
| Macrophage Test No 2: 1 hr. Count | | | | | | |
| Well (total Volume added 30 uL) | | | | | | |
| Blank (2XBB) | 300 | 300 | 0 | 0 | 0.00% | 0.00 |
| Tosyl-MBs | 300 | 273 | 52 | 0.17333333 | 9.00% | 0.02 |
| PDGA-MBs | 300 | 272 | 67 | 0.22 | 9.33% | 0.02 |
| Tosyl + FcApt | 300 | 218 | 139 | 0.46 | 27.33% | 0.13 |
| PDGA + FcApt | 300 | 187 | 243 | 0.81 | 37.67% | 0.31 |
| Macrophage Test No. 3: 1 hr. Count | | | | | | |
| Well (total Volume added 60 uL) | | | | | | |
| Blank | 300 | 300 | 0 | 0.00 | 0.00% | 0.00 |
| 2-Tosyl | 300 | 246 | 83 | 0.28 | 18.00% | 0.05 |
| 3-PDGA | 300 | 246 | 116 | 0.39 | 18.00% | 0.07 |
| Tosyl + FcApt | 300 | 252 | 116 | 0.39 | 16.00% | 0.06 |
| PDGA + FcApt | 300 | 206 | 195 | 0.65 | 31.33% | 0.20 |
| Macrophage Test No. 3: 2 hr. count | | | | | | |
| Well (total Volume added 60 uL) | | | | | | |
| Blank (2XBB) | 300 | 300 | 0 | 0.00 | 0.00% | 0.00 |
| Tosyl | 300 | 186 | 512 | 1.71 | 38.00% | 0.65 |
| PDGA | 300 | 158 | 256 | 0.85 | 47.33% | 0.40 |
| Tosyl + FcApt | 300 | 212 | 264 | 0.88 | 29.33% | 0.26 |
| PDGA + FcApt | 300 | 136 | 498 | 1.66 | 54.67% | 0.91 |
| Macrophage Test No. 3: 24 hr. count | | | | | | |
| Well (total Volume added 60 uL) | | | | | | |
| Blank (2XBB) | 300 | 300 | 0 | 0.00 | 0.00% | 0.00 |
| Tosyl-MB | 300 | 44 | 676 | 2.25 | 85.33% | 1.92 |
| PDGA-MB | 300 | 53 | 628 | 2.09 | 82.33% | 1.72 |
| Tosyl + FcApt | 300 | 92 | 854 | 2.85 | 69.33% | 1.97 |
| PDGA + FcApt | 300 | 52 | 804 | 2.68 | 82.67% | 2.22 |

Example 5

Aptamer Sequences

The following Aptamer clones were identified as disclosed herein following the sequences.

All of the following sequences are listed from 5' to 3' from left to right.

Anti-Botulinum Toxin A and B Aptamers
Developed Against the Holotoxins (HT)
and Light Chains (LC)

| Aptamer Clone | DNA sequence |
|---|---|
| BoNT A/B HT | CATCCGTCACACCTGCTCTGCTATCACATGCCTGCTGAAGTGGTGTTGGCTCCCGTATCA (SEQ ID NO: 1) |
| BoNT A/B LC | CATCCGTCACACCTGCTCTGATCAGGGAAGACGCCAACACTGGTGTTGGCTCCCGTATCA (SEQ ID NO: 2) |

| Campylobacter jejuni MgCl₂-Extracted Surface Antigen Aptamer Sequences | |
|---|---|
| Aptamer Clone | DNA sequence |
| Campylobacter jejuni 1 | CATCCGTCACACCTGCTCTGGGGAGGGTGGCGCCCGT CTCGGTGGTGTTGGCTCCCGTATCA (SEQ ID NO: 3) |
| Campylobacter jejuni 2 | CATCCGTCACACCTGCTCTGGGATAGGGTCTCGTGCT AGATGTGGTGTTGGCTCCCGTATCA (SEQ ID NO: 4) |
| Campylobacter jejuni 3 | CATCCGTCACACCTGCTCTGGACCGGCGCTTATTCCT GCTTGTGGTGTTGGCTCCCGTATCA (SEQ ID NO: 5) |
| Campylobacter jejuni 4 | CATCCGTCACACCTGCYCTGGAGCTGATATTGGATGG TCCGGTGGTGTTGGCTCCCGTATCA (SEQ ID NO: 6) |
| Campylobacter jejuni 5 | CATCCGTCACACCTGCYCYGCCCAGAGCAGGTGTGAC GGATGTGGTGTTGGCTCCCGTATCA (SEQ ID NO: 7) |
| Campylobacter jejuni 6 | CATCCGTCACACCTGCYCYGCCGACCATCCAATATC AGCTGTGGTGTTGGCTCCCGTATCA (SEQ ID NO: 8) |

| PDGA Aptamer Sequences | |
|---|---|
| Aptamer Clone | DNA sequence |
| PDGA 2 M13F | CATCCGTCACACCTGCTCTGGTTCGCCCCGGTCAAGGAG AGTGGTGTTGGCTCCCGTATC (SEQ ID NO: 9) |
| PDGA 2 M13R | GATACGGGAGCCAACACCACTCTCCTTGACCGGGGCGAA CCAGAGCAGGTGTGACGGATG (SEQ ID NO: 10) |
| PDGA 5 M13F | CATCCGTCACACCTGCTCTGGATAAGATCAGCAACAAGT TAGTGGTGTTGGCTCCCGTATC (SEQ ID NO: 11) |
| PDGA 5 M13R | GATACGGGAGCCAACACCACTAACTTGTTGCTGATCTTA TCAGAGCAGGTGTGACGGATG (SEQ ID NO: 12) |

| Small Molecule Aptamer Sequences | |
|---|---|
| Atamer Clone | DNA Sequence |
| Acetylcholine 25F | ATACGGGAGCCAACACCA-TCATTTGCAAATATG AATTCCACTTAAAGAAATTCA-AGAGCAGGTGTG ACGGAT (SEQ ID NO: 13) |
| Acetylcholine 25R | ATCCGTCACACCTGCTCT-TGAATTTCTTTAAGT GGAATTCATATTTGCAAATGA-TGGTGTTGGCTC CCGTAT (SEQ ID NO: 19) |
| Diazinon 12F | ATACGGGAGCCAACACCA-TTAAATCAATTGTGC CGTGTTGGTCTTGTCTCATCG-AGAGCAGGTGTG ACGGAT (SEQ ID NO: 14) |
| Diazinon 12R | ATCCGTCACACCTGCTCT-CGATGAGACAAGACC AACACGGCACAATTGATTTAA-TGGTGTTGGCTC CCGTAT (SEQ ID NO: 23) |
| Diazinon 17F | ATACGGGAGCCAACACCA-TTTTTATTATCGGTA TGATCCTACGAGTTCCTCCCA-AGAGCAGGTGTG ACGGAT (SEQ ID NO: 15) |
| Diazinon 17R | ATCCGTCACACCTGCTCT-TGGGAGGAACTCGTA GGATCATACCGATAATAAAAA-TGGTGTTGGCTC CCGTAT (SEQ ID NO: 24) |
| Diazinon 18F | ATACGGGAGCCAACACCA-CCGTATATCTTATTA TGCACAGCATCACGAAAGTGC-AGAGCAGGTGTG ACGGAT (SEQ ID NO: 16) |
| Diazinon 18R | ATCCGTCACACCTGCTCT-TTTTTATTATCGGTA TGATCCTACGAGTTCCTCCCA-TGGTGTTGGCTC CCGTAT (SEQ ID NO: 25) |
| Diazinon 19F | ATACGGGAGCCAACACCA-TTAACGTTAAGCGGC CTCACTTCTTTTAATCCTTTC-AGAGCAGGTGTG ACGGAT (SEQ ID NO: 17) |
| Diazinon 19R | ATCCGTCACACCTGCTCT-GAAAGGATTAAAAGA AGTGAGGCCGCTTAACGTTAA-TGGTGTTGGCTC CCGTAT (SEQ ID NO: 26) |
| Diazinon 20F | ATCCGTCACACCTGCTCT-AATATAGAGGTATTG CTCTTGGACAAGGTACAGGGA-TGGTGTTGGCTC CCGTAT (SEQ ID NO: 18) |
| Diazinon 20R | ATACGGGAGCCAACACCA-TCCCTGTACCTTGTC CAAGAGCAATACCTCTATATT-ACCACAACCGAG GGCATA (SEQ ID NO: 27) |
| Malathion 17F | ATACGGGAGCCAACACCA-GCAGTCAAGAAGTTA AGAGAAAAACAATTGTGTATA-AGAGCAGGTGTG ACGGAT (SEQ ID NO: 20) |
| Malathion 17R | ATCCGTCACACCTGCTCT-TATACACAATTGTTT TTCTCTTAACTTCTTGACTGC-TGGTGTTGGCTC CCGTAT (SEQ ID NO: 28) |
| Malathion 21F | ATCCGTCACACCTGCTCT-GCGCCACAAGATTGC GGAAAGACACCCGGGGGGCT-TGGTGTTGGCTCC CGTAT (SEQ ID NO: 21) |
| Malathion 21R | ATACGGGAGCCAACACCA-AGCCCCCCGGGTGTC TTTCCGCAATCTTGTGGCGC-AGAGCAGGTGTGA CGGAT (SEQ ID NO: 29) |
| Malathion 25F | ATCCGTCACACCTGCTCT-GGCCTTATGTAAAGC GTTGGG-TGGTGTTGGCTCCCGTAT (SEQ ID NO: 22) |
| Malathion 25R | ATACGGGAGCCAACACCA-CCCAACGCTTTACAT AAGGCC-AGAGCAGGTGTGACGGAT (SEQ ID NO:30) |

-continued

Small Molecule Aptamer Sequences

| Atamer Clone | DNA Sequence |
|---|---|
| Methylphosphonic Acid (MPA) | ATCCGTCACACCTGCTCT-CGATGAGACAAGAGG AACACGGCACAATTGATTTAA-TGGTGTTGGCTC CCGTAT (SEQ ID NO: 31) |

These aptamers were generally collected from embodiments of the Systematic Evolution of Ligands by EXponential enrichment (SELEX as disclosed in U.S. Pat. No. 5,270,163 cited herein) process. Each of the targets diazinon and malathion has a different attachment chemistry for immobilization. Immobilization is a factor to affinity selection of aptamers from a random library of sequences. Various embodiments of an immobilization approach are outlined in the Table below as taught by Bruno and Kiel (2002).

SEQ ID NOS: 32-50 represent the aforementioned aptamers without primers.

TABLE 6

Immobilization Strategies for Each of the Aptamer Targets

| Target Molecule(s) | Immobilization Strategies | Notes |
|---|---|---|
| Amino-Methylphosphonic acid (Amino-MPA) | Attaches directly to tosyl-MBs | Amino-MPA is readily available from Aldrich Chemical Co. |
| Acetylcholine, Diazinon, and Malathion | Mannich condensation reaction- due to the lack of functional groups, Mannich chemistry is needed | PharmaLink™ Columns have been purchased from Pierce Chemical Co. |
| MPA, isopropyl-MPA, and pinacolyl-MPA | Mannich or Mitsunobu ester formation | Ref: Campbell and Bermak, 1994 |

Aptamer Selection Protocol for Bead-Immobilized Target Molecules

1. SELEX DNA template (72mer; see Table below) is reconstituted in 1 mL of nuclease-free water. Five hundred uL of this template solution (160-180 nanomoles of DNA) is heated to 95° C. for 5 minutes to ensure that the DNA library is single-stranded (ss).
2. The hot template solution is added to 100 µL of target-MBs ($2 \times 10^7$ MBs) with 600 uL of 2× binding buffer (2×BB; 1 M NaCl, 20 mM Tris HCl and 2 mM $MgCl_2$ in nuclease-free deionized sterile water with filter sterilization; pH 7.2-7.4).
3. The DNA library-target-MB suspension (1.2 mL) is mixed in a sterile polypropylene tube at room temperature (RT) for 1 hour.
4. Target-MBs with any bound DNA (round 1 aptamers) are pelleted by use of a strong permanent magnet and, if necessary, a centrifuge.
5. The DNA-target-MBs are washed three times in 0.4 mL of sterile 1×BB (2×BB diluted 1:1 in sterile nuclease-free deionized water).
6. Following the third wash, the MB pellet (about 75 µL) is used in a PCR reaction to amplify the bound DNA as follows: The MB pellet is split into 15 uL aliquots and added to five Molecular BioProducts, Inc. (MBP, San Diego, Calif.) "Easy Start Micro 50™" tubes (Catalogue No. 6020, which contain most of the nonperishable components of a PCR reaction beneath a wax seal). Three µL of 1:10 primer mix (10% primer 1 plus 10% primer 2 by volume in nuclease-free deionized water or approximately 20 nanomoles of each primer per mL; Table) plus 2 µL (10 Units) of Taq DNA polymerase and 5 uL of 20 mM $MgCl_2$ are added to each of the five tubes.
7. PCR is carried out on a Perkin-Elmer GeneAmp2400 thermal cycler. Tubes are subjected to an initial 95° C. phase for 5 minutes followed by 20-40 cycles of 1 minute at 95° C., 1 minute at 53° C., and 1 minute at 72° C. followed by a 72° C. completion phase for 7 minutes and refrigeration at 4° C. This constitutes the first round of SELEX.
8. Ten uL of PCR product from one of the five tubes was used per round for agarose gel electrophoresis to verify the presence of the correct length (72 base) PCR product. Ten uL of PCR product is mixed 1:1 with 5× loading buffer (BioRad, Hercules, Calif.) and loaded into a 2% agarose submarine gel with 2 uL of 10 mg/ml ethidium bromide per 45 mL gel and run at 100V in cold 1×TBE (Tris-Borate-EDTA; BioRad) buffer with 5-10 µL of DNA ladder standard (BioRad) mixed 1:1 with loading buffer.
9. To begin the second round and all subsequent rounds, four complete tubes of the five original PCR tubes are heated to 95° C. for 5 minutes to release all bound DNA (aptamers) from the target protein-MBs. Heating is accomplished in the thermal cycler. The fifth tube is always retained as a backup to the SELEX process and refrigerated.
10. All available DNA is siphoned out of the hot tubes while the tubes sit in the thermal cycler block. Generally about 25 µL of fluid can be siphoned per tube (100 µL from four tubes) without removing the MBs.
11. The 100 µL of hot DNA is added to 100 uL of fresh target protein-MBs ($2 \times 10^7$ MBs) in 200 µL of 2×BB and allowed to mix for 1 hour at RT as in step 3 above, and the process is repeated from that point for the remaining rounds of SELEX. At least four more rounds should be accomplished.

TABLE 7

SELEX Aptamer Template and Primer System Used

| Component | Sequence |
|---|---|
| Template | ATCCGTCACACCTGCTCT-N36-TGGTGTTGGCTCCCGTAT (SEQ ID NO: 51) |
| Primer 1 (Forward) | ATACGGGAGCCAACACCA (SEQ ID NO: 52) |
| Primer 2 (Reverse) | ATCCGTCACACCTGCTCT (SEQ ID NO: 53) |

Notes:
All sequences are shown 5' to 3' from left to right and "N" indicates the randomized region (36 bases long) wherein an equal (25%) chance exists for the base to be A, C, G, or T. All DNA is obtained from Integrated DNA Technologies, Inc. (IDT; Coralville, IA).

PharmaLink™ Column Immobilization for Small Molecule Ligand Coupling

1. Equilibrate a 2 mL PharmaLink gel column (Pierce Chemical Co., Rockford, Ill.) to room temperature (RT) or body temperature (37° C.) as appropriate for aptamer selection. Therapeutic aptamers should generally be selected at 37° C.

2. Remove the top cap and bottom cap sequentially. Remove the caps in this order to prevent the incorporation of bubbles in the gel.
3. Place the column in a sterile 50 mL conical tube.
4. Drain the storage solution.
5. Equilibrate the column with 2×2 mL of 1:3 ethanol: Coupling Buffer and let each aliquot flow through.
6. Replace bottom cap.
7. Dissolve ligand in pure ethanol to its limit of solubility. Notes: Pierce Chemical Co. stated that 1 mL of PharmaLink™ gel has 16-20 umoles of amine linkers per mL of gel. This means that a 2 mL gel can hold 32-40 umoles of ligand. For Diazinon (MW=304.36), the maximum amount per column would be 12.2 mg and for Malathion (MW=330.35), the maximum per column would be 13.2 mg. Hence, dissolve these amounts in 1 mL of pure ethanol and add 3 mL of coupling buffer.
8. Add the ligand solution to the column.
9. Add 200 µL of Coupling Reagent to the column.
10. Resuspend the gel by stirring with a sterile Pasteur pipette or other rod-like instrument.
11. Transfer the gel slurry to a reaction tube and discard the column.
12. Cap the reaction tube. React at 37° C. in the bacterial incubator for a minimum of 24 hrs. Resuspend by stirring periodically.

Transfer Gel Slurry to a New Column
1. Apply bottom cap to an empty column.
2. Add NFW to column until it nearly reaches the top.
3. Set frit on top of NFW and use inverted serum separator to position frit into the bottom of the column.
4. Decant NFW from the column.
5. Resuspend the coupled gel in the reaction tube by swirling and add to the new column.

Column Washing
1. Wash noncoupled ligand from the column with 48 mL of 1:3 ethanol:PharmaLink Wash Buffer (i.e., 12 mL of ethanol added to 36 mL of Wash Buffer).
2. Set top frit in column and slide to within 1 mm of the top of the gel bed.
3. Cap and refrigerate the column until used. Do NOT add azide as this may react with the ligand.

Aptamer Generation Using PharmaLink™ Columns

1. Reconstitute DNA template (≧160 nanomoles of 60mer in 1 mL of 1× binding buffer (1×BB: 0.5 M NaCl, 10 mM Tris HCl and 1 mM $MgCl_2$ in nuclease-free deionized sterile water (NFW), pH 7.2-7.4). See Bruno & Kiel (2002)
2. Heat the 1 mL of template solution at 95° C. for 5 minutes to ensure DNA is single-stranded.
3. Equilibrate a Pierce PharmaLink™ column (Cat. No. 44930) with immobilized target molecules in it with 6 mL of 1×BB.
4. Add hot DNA library to the column, allow it to percolate through and bind for 1 hour at room temperature (RT). Note: 1 mL is the void volume of the column and will therefore expel exactly the correct amount of fluid to fill the length of the column with the DNA template solution. Stop the column flow by capping it when the DNA solution has completely entered the column and the top of the column just turns dry.
5. Wash unbound DNA out of column in a total of 16 mL of 1×BB.
6. Cap the column exit port and pre-heat the column to 60° C. in an incubator or water bath for 10-15 minutes.
7. Elute bound DNA by addition of 1 mL volume of 3 M sodium acetate at pH 5.2, which is allowed to interact with the column for 10 minutes by stopping the flow after the 3 M sodium acetate has percolated fully into the column bed. Note: Hot nuclease free water failed to liberate much DNA from the column and 0.3 M sodium acetate at pH 5.2 can be used, but it is much less efficient and requires much higher volumes (8-12 mL).
8. Elute the DNA with an additional 1 mL of 1×BB added to the top of the column. Thereafter, flush the column liberally with 1×BB, cap and store in the refrigerator.
9. Obtain $A_{260nm}$ of the eluted DNA fractions. Absorbance readings of the eluate at 260 nm should generally be >0.100.
10. Prepare primer-conjugated magnetic microbeads (MBs) by heating 400 uL (approximately 12 to 50 ug) of each the 5'-biotinylated 18mer SELEX primers (forward and reverse or primers 1 and 2) described below to 95° C. for 5 min and adding the hot biotinylated primers to 800 uL (8 mg) of Dynal streptavidin-coated M280 (2.8 um diameter) MBs.
11. Collect the primer-MBs with a strong permanent magnet and wash them several times in 1-2 mL volumes of 1×BB.
12. Reconstitute the primer-MBs in 1 mL of 1×BB and add 100 uL to the 20 mL of diluted DNA eluted from the column. This process is referred to as "fishing" for DNA aptamers.
13. Mix the primer-MBs with the 20 mL of eluted DNA for 2 hrs at room temperature
14. Collect the DNA-primer-MBs by means of a strong permanent magnet.
15. Reconstitute the DNA to 75 µL with NFW.
16. Add 15 µL reconstituted DNA to each of 5 Easy Start Micro 50™ tubes, plus 3 µL primer mix (1:10 each 5'-biotin-primer in NFW), 2 µL (10 U) of Takara ExTaq™ or other Taq DNA polymerase, 5 uL 20 mM $MgCl_2$, and enough NFW to bring each tube's total volume to 50 uL.
17. Perform 40 cycles of PCR amplification per the following profile:
   i. 5 min at 95° C., (40 cycles of: 1 min at 95° C., 1 min at 53° C., and 1 min at 72° C.), 7 min at 72° C. and hold at 4° C.
   ii. This constitutes the first round of SELEX.
18. Use 10 µL of PCR product from one tube to verify correct length (60 base) by agarose gel electrophoresis. Mix 10 µL of PCR product in 1:1 ratio with 5× loading buffer (BioRad) and load into 2% agarose submarine gel (containing 2 µL of 10 mg/mL ethidium bromide per 45 mL gel). Run electrophoresis at 100V in cold 1× TBE buffer (Tris-Borate-EDTA; BioRad) with 5 µL DNA ladder standard mixed 1:1 with 5× loading buffer.
19. To begin second and all subsequent rounds, heat two of five PCR tubes from previous round to 95° C. for 5 minutes (retain other tubes as a back-up).
20. Aspirate 100 µL hot ssDNA out of tubes (which remain in thermal cycler heat-block) and add to 900 µL of 1×BB.
21. Heat the 1 mL of DNA solution to 95° C. for 5 minutes.
22. Add hot DNA to column and repeat steps 4-17 for the remaining rounds of SELEX (4-5 rounds minimum should be attempted).
23. If columns do not appear damaged, they may be reused. Therefore, rinse the column with at least 10 mL of 1×BB and store at 4° C. until needed again.

REFERENCES

U.S. Pat. No. 5,270,163 et seq., U.S. Pat. No. 5,475,096, U.S. Pat. No. 6,566,343, U.S. Pat. No. 6,623,926.
Alderson T. Mutat Res. 154:101-110, 1985.
Anorbe M. G., et al. Chem. Eur. J. 10:1046-1057, 2004.
Bell, et al. In Vitro Cell Devlop. Biol. Animal. 35:533-542, 1999.
Bruno and Kiel. BioTechniques. 32:178-183, 2002.
Bruno J. G. Biochem. Biophys. Res. Comm. 234:117-120, 1997.
Chu T. C., et al. Cancer Res. 66:5989-5992, 2006.
Dolan P. L., et al. Nucleic Acids Res. 29:e107, 2001.
Dougan H., et al. Nuclear Med. Biol. 27:289-297, 2000.
Gacesa P. and Whish W. J. D. Biochem. J. 175:349-352, 1978.
Gavrilova E. M. et al. Biokhimiia. 46:306-313, 1981.
Harrison G. S., et al. Molec. Cell Biol. 6:2364-2370, 1986.
Hayatsu H., et al. Nucleic Acids res. 10:6281-6293, 1982.
Hopwood J. Histochem. J. 7:267-276, 1975.
Kloepfer J. A., et al. Appl. Environ. Microbiol. 71:2548-2557, 2005.
Matsuura K., et al. Bioconj. Chem. 11:202-211, 2000.
Murphy, et al. Nucleic Acids Res. 31:e110-e118, 2003.
Ono, et al. Nucleic. Acids Res. 25:4581-4588. 1997.
Pues H., et al. Biochemistry. 38:1426-1434, 1999.
Rall T. W. and Lehne R. A. J. Cyclic Nucleotide Res. 8:243-265, 1982.
Scavetta R. D., et al. Nucleic Acids Res. 28:3950-3961, 2000.
Ulrich, et al. J. Biol. Chem. 277:20756-20762, 2002.
Wang H., et al. Biochemistry. 44:11295-11306, 2005.
Welkos, et al., Microbiology. 147:1677-1685, 2001.
Yamazaki Y. and Suzuki H. Eur. J. Biochem. 92:197-207, 1978.
Zhou M. Y. and Gomez-Sanchez C. E. Curr. Issues Mol. Biol. 2:1-7, 2000.
Zinoviev V. V., et al. Biol. Chem. 379:481-488, 1998.

---

What is claimed is:

1. An aptamer having a 3' overhang of adenine, cytosine or guanine deoxynucleotides to which a protein conjugate is operatively coupled to form an aptamer-3'-conjugate; wherein said aptamer is selected from SEQ ID NO: 1 and further wherein, the protein conjugate is a biocidal protein or a serum-stabilizing protein.

2. The aptamer-conjugate of claim 1, wherein said biocidal protein is a phage lysis protein, a protein that recruits the cells of immune system, or a protein that activates the immune system.

3. The aptamer-conjugate of claim 1, wherein said serum-stabilizing protein is serum albumin or human serum albumin.

4. The aptamer-conjugate of claim 3, wherein said aptamer-conjugate binds to a toxin and neutralizes its effect.

5. The aptamer-conjugate of claim 4, wherein said toxin is selected from the group consisting of bacterial biotoxins, botulinum toxins, cholera toxin, ricin, staphylococcal enterotoxins, plant toxins, insect toxin, arachnid toxin, or reptilian venoms.

6. The aptamer-conjugate of claim 1, wherein said aptamer-conjugate is therapeutic.

7. A method of killing a pathogen, the method comprising the steps of:
   a) providing a target pathogen in vitro, wherein the target pathogen is *E. coli;*
   b) contacting the target pathogen with an anti-LPS aptamer, wherein the aptamer binds to the target pathogen and is bound to a biocide conjugate that prevents the target pathogen from reproducing; and
   c) killing the aptamer-bound target pathogen.

8. The method of claim 7, wherein the biocide conjugate kills said target pathogen.

9. The method of claim 7, wherein the biocide conjugate is selected from the group consisting of C1qrs, Fc, and C3b.

10. The method of claim 7, wherein the biocide conjugate is a nanotube.

11. A method of neutralizing a toxin, the method comprising the steps of:
   a) providing a toxin in vitro, wherein the toxin is botulinum toxin A;
   b) contacting the toxin with an anti-botulinum toxin A aptamer, wherein the aptamer binds to the toxin; and
   c) neutralizing the toxin.

* * * * *

SEQUENCE LISTING

```
<160> NUMBER OF SEQ ID NOS: 53

<210> SEQ ID NO 1
<211> LENGTH: 60
<212> TYPE: DNA
<213> ORGANISM: Artificial Sequence
<220> FEATURE:
<223> OTHER INFORMATION: Synthesized Oligonucleotide Sequence

<400> SEQUENCE: 1
catccgtcac acctgctctg ctatcacatg cctgctgaag tggtgttggc tcccgtatca          60

<210> SEQ ID NO 2
<211> LENGTH: 60
<212> TYPE: DNA
<213> ORGANISM: Artificial Sequence
<220> FEATURE:
<223> OTHER INFORMATION: Synthesized Oligonucleotide Sequence

<400> SEQUENCE: 2
catccgtcac acctgctctg atcagggaag acgccaacac tggtgttggc tcccgtatca          60

<210> SEQ ID NO 3
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 3
catccgtcac acctgctctg gggagggtgg cgcccgtctc ggtggtgttg gctcccgtat          60
ca                                                                         62

<210> SEQ ID NO 4
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 4
catccgtcac acctgctctg ggatagggtc tcgtgctaga tgtggtgttg gctcccgtat          60
ca                                                                         62
```

```
<210> SEQ ID NO 5
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 5
catccgtcac acctgctctg gaccggcgct tattcctgct tgtggtgttg gctcccgtat      60
ca                                                                    62

<210> SEQ ID NO 6
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 6
catccgtcac acctgcyctg gagctgatat tggatggtcc ggtggtgttg gctcccgtat      60
ca                                                                    62

<210> SEQ ID NO 7
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 7
catccgtcac acctgcycyg cccagagcag gtgtgacgga tgtggtgttg gctcccgtat      60
ca                                                                    62

<210> SEQ ID NO 8
<211> LENGTH: 62
<212> TYPE: DNA
<213> ORGANISM: Artificial Sequence
<220> FEATURE:
<223> OTHER INFORMATION: Synthesized Oligonucleotide Sequence

<400> SEQUENCE: 8
catccgtcac acctgcycyg ccggaccatc caatatcagc tgtggtgttg gctcccgtat      60
ca                                                                    62

<210> SEQ ID NO 9
<211> LENGTH: 60
<212> TYPE: DNA
<213> ORGANISM: Artificial Sequence
<220> FEATURE:
<223> OTHER INFORMATION: Synthesized Oligonucleotide Sequence

<400> SEQUENCE: 9
catccgtcac acctgctctg gttcgccccg gtcaaggaga gtggtgttgg ctcccgtatc      60

<210> SEQ ID NO 10
<211> LENGTH: 60
<212> TYPE: DNA
<213> ORGANISM: Artificial Sequence
<220> FEATURE:
<223> OTHER INFORMATION: Synhesized Oligonucleotide Sequence

<400> SEQUENCE: 10
gatacgggag ccaacaccac tctccttgac cggggcgaac cagagcaggt gtgacggatg      60
```

```
<210> SEQ ID NO 11
<211> LENGTH: 61
<212> TYPE: DNA
<213> ORGANISM: Artificial Sequence
<220> FEATURE:
<223> OTHER INFORMATION: Synthesized Oligonucleotide Sequence

<400> SEQUENCE: 11
catccgtcac acctgctctg gataagatca gcaacaagtt agtggtgttg gctcccgtat      60
c                                                                     61

<210> SEQ ID NO 12
<211> LENGTH: 60
<212> TYPE: DNA
<213> ORGANISM: Artificial Sequence
<220> FEATURE:
<223> OTHER INFORMATION: Synthesized Oligonucleotide Sequence

<400> SEQUENCE: 12
gatacgggag ccaacaccac taacttgttg ctgatcttat cagagcaggt gtgacggatg      60

<210> SEQ ID NO 13
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 13
atacgggagc caacaccatc atttgcaaat atgaattcca cttaaagaaa ttcaagagca      60
ggtgtgacgg at                                                         72

<210> SEQ ID NO 14
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 14
atacgggagc caacaccatt aaatcaattg tgccgtgttg gtcttgtctc atcgagagca      60
ggtgtgacgg at                                                         72

<210> SEQ ID NO 15
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 15
atacgggagc caacaccatt tttattatcg gtatgatcct acgagttcct cccaagagca      60
ggtgtgacgg at                                                         72

<210> SEQ ID NO 16
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 16
atacgggagc caacaccacc gtatatctta ttatgcacag catcacgaaa gtgcagagca      60
ggtgtgacgg at                                                         72
```

<210> SEQ ID NO 17
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 17
atacgggagc caacaccatt aacgttaagc ggcctcactt cttttaatcc tttcagagca    60
ggtgtgacgg at    72

<210> SEQ ID NO 18
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 18
atccgtcaca cctgctctaa tatagaggta ttgctcttgg acaaggtaca gggatggtgt    60
tggctcccgt at    72

<210> SEQ ID NO 19
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 19
atccgtcaca cctgctcttg aatttctttä agtggaattc atatttgcaa atgatggtgt    60
tggctcccgt at    72

<210> SEQ ID NO 20
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 20
atacgggagc caacaccagc agtcaagaag ttaagagaaa aacaattgtg tataagagca    60
ggtgtgacgg at    72

<210> SEQ ID NO 21
<211> LENGTH: 71
<212> TYPE: DNA
<213> ORGANISM: Artificial Sequence
<220> FEATURE:
<223> OTHER INFORMATION: Synthesized Oligonucleotide Sequence

<400> SEQUENCE: 21
atccgtcaca cctgctctgc gccacaagat tgcggaaaga cacccggggg cttggtgtt    60 ggctcccgta t    71

<210> SEQ ID NO 22
<211> LENGTH: 57
<212> TYPE: DNA
<213> ORGANISM: Artificial Sequence
<220> FEATURE:
<223> OTHER INFORMATION: Synthesized Oligonucleotide Sequence

<400> SEQUENCE: 22

```
atccgtcaca cctgctctgg ccttatgtaa agcgttgggt ggtgttggct cccgtat      57
```

<210> SEQ ID NO 23
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 23

```
atccgtcaca cctgctctcg atgagacaag accaacacgg cacaattgat ttaatggtgt    60
tggctcccgt at                                                        72
```

<210> SEQ ID NO 24
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 24

```
atccgtcaca cctgctcttg ggaggaactc gtaggatcat accgataata aaaatggtgt    60
tggctcccgt at                                                        72
```

<210> SEQ ID NO 25
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 25

```
atccgtcaca cctgctcttt tttattatcg gtatgatcct acgagttcct cccatggtgt    60
tggctcccgt at                                                        72
```

<210> SEQ ID NO 26
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 26

```
atccgtcaca cctgctctga aaggattaaa agaagtgagg ccgcttaacg ttaatggtgt    60
tggctcccgt at                                                        72
```

<210> SEQ ID NO 27
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 27

```
atacgggagc caacaccatc cctgtacctt gtccaagagc aatacctcta tattaccaca    60
accgagggca ta                                                        72
```

<210> SEQ ID NO 28
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 28
atccgtcaca cctgctctta tacacaattg tttttctctt aacttcttga ctgctggtgt    60
tggctcccgt at    72

<210> SEQ ID NO 29
<211> LENGTH: 71
<212> TYPE: DNA
<213> ORGANISM: Artificial Sequence
<220> FEATURE:
<223> OTHER INFORMATION: Synthesized Oligonucleotide Sequence

<400> SEQUENCE: 29
atacgggagc caacaccaag ccccccgggt gtctttccgc aatcttgtgg cgcagagcag    60
gtgtgacgga t    71

<210> SEQ ID NO 30
<211> LENGTH: 57
<212> TYPE: DNA
<213> ORGANISM: Artificial Sequence
<220> FEATURE:
<223> OTHER INFORMATION: Synthesized Oligonucleotide Sequence

<400> SEQUENCE: 30
atacgggagc caacaccacc caacgcttta cataaggcca gagcaggtgt gacggat    57

<210> SEQ ID NO 31
<211> LENGTH: 72
<212> TYPE: DNA
<213> ORGANISM: Artificial Sequence
<220> FEATURE:
<223> OTHER INFORMATION: Synthesized Oligonucleotide Sequence

<400> SEQUENCE: 31
atccgtcaca cctgctctcg atgagacaag aggaacacgg cacaattgat ttaatggtgt    60
tggctcccgt at    72

<210> SEQ ID NO 32
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 32
tcatttgcaa atatgaattc cacttaaaga aattca    36

<210> SEQ ID NO 33
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 33
ttaaatcaat tgtgccgtgt tggtcttgtc tcatcg    36

<210> SEQ ID NO 34
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 34

-continued tttttattat cggtatgatc ctacgagttc ctccca                               36

<210> SEQ ID NO 35
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 35
ccgtatatct tattatgcac agcatcacga aagtgc                               36

<210> SEQ ID NO 36
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 36
ttaacgttaa gcggcctcac ttcttttaat cctttc                               36

<210> SEQ ID NO 37
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 37
aatatagagg tattgctctt ggacaaggta caggga                               36

<210> SEQ ID NO 38
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 38
tgaatttctt taagtggaat tcatatttgc aaatga                               36

<210> SEQ ID NO 39
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 39
gcagtcaaga agttaagaga aaacaattg tgtata                                36

<210> SEQ ID NO 40
<211> LENGTH: 35
<212> TYPE: DNA
<213> ORGANISM: Artificial Sequence
<220> FEATURE:
<223> OTHER INFORMATION: Synthesized Oligonucleotide Sequence

<400> SEQUENCE: 40
gcgccacaag attgcggaaa gacacccggg gggct                                35

<210> SEQ ID NO 41
<211> LENGTH: 21
<212> TYPE: DNA
<213> ORGANISM: Artificial Sequence

```
<220> FEATURE:
<223> OTHER INFORMATION: Synthesized Oligonucleotide Sequence

<400> SEQUENCE: 41
ggccttatgt aaagcgttgg g                                              21

<210> SEQ ID NO 42
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 42
cgatgagaca agaccaacac ggcacaattg atttaa                              36

<210> SEQ ID NO 43
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 43
tgggaggaac tcgtaggatc ataccgataa taaaaa                              36

<210> SEQ ID NO 44
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 44
tttttattat cggtatgatc ctacgagttc ctccca                              36

<210> SEQ ID NO 45
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 45
gaaaggatta aagaagtga ggccgcttaa cgttaa                               36

<210> SEQ ID NO 46
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 46
tccctgtacc ttgtccaaga gcaatacctc tatatt                              36

<210> SEQ ID NO 47
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 47
tatacacaat tgtttttctc ttaacttctt gactgc                              36
```

```
<210> SEQ ID NO 48
<211> LENGTH: 35
<212> TYPE: DNA
<213> ORGANISM: Artificial Sequence
<220> FEATURE:
<223> OTHER INFORMATION: Synthesized Oligonucleotide Sequence

<400> SEQUENCE: 48
agccccccgg gtgtctttcc gcaatcttgt ggcgc                              35

<210> SEQ ID NO 49
<211> LENGTH: 21
<212> TYPE: DNA
<213> ORGANISM: Artificial Sequence
<220> FEATURE:
<223> OTHER INFORMATION: Synthesized Oligonucleotide Sequence

<400> SEQUENCE: 49
cccaacgctt tacataaggc c                                             21

<210> SEQ ID NO 50
<211> LENGTH: 36
<212> TYPE: DNA
<213> ORGANISM: Artificial Sequence
<220> FEATURE:
<223> OTHER INFORMATION: Synthesized Oligonucleotide Sequence

<400> SEQUENCE: 50
cgatgagaca agaggaacac ggcacaattg atttaa                             36

<210> SEQ ID NO 51
<211> LENGTH: 72
<212> TYPE: DNA
<213> ORGANISM: Artificial Sequence
<220> FEATURE:
<223> OTHER INFORMATION: Synthesized Oligonucleotide Sequence
<220> FEATURE:
<221> NAME/KEY: misc_feature
<222> LOCATION: (19)..(54)
<223> OTHER INFORMATION: n is a, c, g, or t

<400> SEQUENCE: 51
atccgtcaca cctgctctnn nnnnnnnnnn nnnnnnnnnn nnnnnnnnnn nnntggtgt    60 tggctcccgt at                                                       72

<210> SEQ ID NO 52
<211> LENGTH: 18
<212> TYPE: DNA
<213> ORGANISM: Artificial Sequence
<220> FEATURE:
<223> OTHER INFORMATION: Synthesized Oligonucleotide Sequence

<400> SEQUENCE: 52
atacgggagc caacacca                                                 18

<210> SEQ ID NO 53
<211> LENGTH: 18
<212> TYPE: DNA
<213> ORGANISM: Artificial Sequence
<220> FEATURE:
<223> OTHER INFORMATION: Synthesized Oligonucleotide Sequence

<400> SEQUENCE: 53
atccgtcaca cctgctct                                                 18
```